US008431118B2

(12) United States Patent
Lai et al.

(10) Patent No.: US 8,431,118 B2
(45) Date of Patent: Apr. 30, 2013

(54) ANTI-HERPES SIMPLEX VIRUS ANTIBODIES AND METHODS OF USE THEREOF

(75) Inventors: Jiann-Shiun Lai, Xizhi (TW); Woan-Eng Chan, Xizhi (TW)

(73) Assignee: DCB-USA LLC, Wilmington, DE (US)

(*) Notice: Subject to any disclaimer, the term of this patent is extended or adjusted under 35 U.S.C. 154(b) by 0 days.

(21) Appl. No.: 13/546,967

(22) Filed: Jul. 11, 2012

(65) Prior Publication Data
US 2012/0282260 A1 Nov. 8, 2012

Related U.S. Application Data

(60) Division of application No. 12/651,325, filed on Dec. 31, 2009, now Pat. No. 8,252,906, which is a continuation-in-part of application No. 12/348,550, filed on Jan. 5, 2009, now abandoned.

(51) Int. Cl.
*A61K 49/16* (2006.01)
*A61K 39/245* (2006.01)

(52) U.S. Cl.
USPC ........................................ 424/93.1; 424/229.1

(58) Field of Classification Search ................... None
See application file for complete search history.

(56) References Cited

U.S. PATENT DOCUMENTS

| 5,654,174 A | 8/1997 | Cohen et al. |
| 7,060,799 B2 | 6/2006 | Burton et al. |
| 2010/0172906 A1 | 7/2010 | Lai et al. |

FOREIGN PATENT DOCUMENTS

| WO | WO-86/01517 A1 | 3/1986 |
| WO | WO-97/26329 A1 | 7/1997 |
| WO | 2005/011580 A2 | 2/2005 |

OTHER PUBLICATIONS

Almagro, J.C. (2004). "Identification of Differences in the Specificity-Determining Residues of Antibodies that Recognize Antigens of Different Size: Implications for the Rational Design of Antibody Repertoires," *Journal of Molecular Recognition* 17:132-143.
Brown et al. (May 1996) "Tolerance to Single, but Not Multiple, Amino Acid Replacements in Antibody $V_h$ CDR2," *J. Immunol.* 156(9):3285-3291.
Burioni, R. et al. (Jan. 1994). "Recombinant Human Fab to Glycoprotein D Neutralizes Infectivity and Prevents Cell-to-Cell Transmission of Herpes Simplex Viruses 1 and 2 in vitro," *Proc. Natl. Acad. Sci. USA* 91:355-359.
Carfi, A. et al. (Jul. 2001). "Herpes Simplex Virus Glycoprotein D Bound to the Human Receptor HveA," *Molecular Cell* 8:169-179.
Casset et al. (2003). "A Peptide Mimetic of an Anti-CD4 Monoclonal Antibody by Rational Design," *BBRC* (2003) 307, 198-205.
Connolly, S.A. et al. (Jan. 2005). "Potential Nectin-1 Binding Site on Herpes Simplex Virus Glycoprotein D," *Journal of Virology* 79(2):1282-1295.
De Logu, A. et al. (Nov. 1998). "Characterization of a Type-Common Human Recombinant Monoclonal Antibody to Herpes Simplex Virus with High Therapeutic Potential," *Journal of Clinical Microbiology* 36(11):3198-3204.
De Pascallis et al. (2002). "Grafting of "Abbreviated" Complementarity-Determining Regions Containing Specificity-Determining Residues Essential for Ligand Contact to Engineer a Less Immunogenic Humanized Monoclonal Antibody," *The Journal of Immunology* (2002) 169:3076-3084.
Eisenberg, R.J. et al. (Feb. 1985). "Localization of Epitopes of Herpes Simplex Virus Type 1 Glycoprotein D," *Journal of Virology* 52(2):634-644.
Eisenberg, R.J. et al. (1985). "Localization of Epitopes of Herpes Simplex Virus Type 1 Glycoprotein D," *J. Virol.* 53(2): 634-642.
Fuller, A.O. et al. (Aug. 1985). "Specificities of Monoclonal and Polyclonal Antibodies That Inhibit Adsorption of Herpes Simplex Virus to Cells and Lack of Inhibition by Potent Neutralizing Antibodies," *Journal of Virology* 55(2):475-482.
Gonzales, N.R. et al. (e-pub Jun. 17, 2004). "SDR Grafting of a Murine Antibody Using Multiple Human Germline Templates to Minimize its Immunogenicity," *Molecular Immunology* 41:863-872.
Highlander, S.L. et al. (Nov. 1987). "Neutralizing Monoclonal Antibodies Specific for Herpes Simplex Virus Glycoprotein D Inhibit Virus Penetration," *Journal of Virology* 61(11):3356-3364.
International Search Report mailed on Feb. 15, 2010, for PCT Patent Application No. PCT/US2009/069952, filed on Dec. 31, 2009, 5 pages.
Kashmiri, S.V.S. et al. (2005). "SDR Grafting—A New Approach to Antibody Humanization," *Methods* 36:25-34.
MacCallum, R.M. et al. (1996). "Antibody-Antigen Interactions: Contact Analysis and Binding Site Topography," *J. Mol. Biol* 262:732-745.
Mannini-Palenzona, A. et al. (Jan. 1998). "Growth, Spread, and Extracellular Localization of Herpes Simplex Virus 1 in Vero Cells in the Presence of an Anti-gD Plague Inhibiting Monoclonal Antibody," *New Microbiologica* 21(1):65-76.
Nicola, A.V. et al. (Apr. 1997). "Antigenic Structure of Soluble Herpes Simplex Virus (HSV) Glycoprotein D Correlates with Inhibition of HSV Infection," *Journal of Virology* 71(4):2940-2946.
Nicola, A.V. et al. (May 1998). "Monoclonal Antibodies to Distinct Sites on Herpes Simplex Virus (HSV) Glycoprotein D Block HSV Binding to HVEM," *Journal of Virology* 72(5):3595-3601.
Reichmann, L. et al. (Mar. 24, 1988). "Reshaping Human Antibodies for Therapy," *Nature* 332: 323-327.
Sanna, P.P. et al. (1996). "Protection of Nude Mice by Passive Immunization with a Type-Common Human Recombinant Monoclonal Antibody Against HSV," *Virology* 215(0011):101-106.
Spear, P.G. et al. (2000). "Three Classes of Cell Surface Receptors for Alphaherpesvirus Entry," *Virology* 275:1-8.
Spear, P.G. (2004). "Herpes Simplex Virus: Receptors and Ligands for Cell Entry," *Cellular Microbiology* 6(5):401-410.
Vajdos, F.F. et al. (Jul. 5, 2002). "Comprehensive Functional Maps of the Antigen-Binding Site of an Anti-ErbB2 Antibody Obtained with Shotgun Scanning Mutagenesis," *J Mol Biol* 320(2):415-428.

(Continued)

*Primary Examiner* — Bao Li
(74) *Attorney, Agent, or Firm* — Morrison & Foerster LLP

(57) ABSTRACT

The invention provides antibodies and polypeptides that specifically bind to the glycoprotein D of herpes simplex virus (HSV) and use of the antibodies and polypeptides for treating or diagnosing HSV infections.

17 Claims, 5 Drawing Sheets

OTHER PUBLICATIONS

Written Opinion of the International Searching Authority mailed on Feb. 15, 2010, for PCT Patent Application No. PCT/US2009/069952, filed on Dec. 31, 2009, 4 pages.

Chen et al., "Prevention of Genital Herpes in a Guinea Pig Model using a Glycoprotein D-Specific Single Chain Antibody as a Microbicide", Virology Journal, BioMed Central, vol. 1, No. 11, Nov. 23, 2004, pp. 1-10.

Minson et al., "An Analysis of the Biological Properties of Monoclonal Antibodies against Glycoprotein D of Herpes Simplex Virus and Identification of Amino Acid Substitutions that Confer Resistance to Neutralization", Journal of General Virology, vol. 67, 1986, pp. 1001-1013.

Muggeridge et al., "Antigenic Analysis of a Major Neutralization Site of Herpes Simplex Virus Glycoprotein D, Using Deletion Mutants and Monoclonal Antibody-Resistant Mutants", Journal of Virology, vol. 62, No. 9, Sep. 1988, pp. 3274-3280.

Muggeridge et al., "Antigenic and Functional Analysis of a Neutralization Site of HSV-1 Glycoprotein D", Virology, vol. 174, 1990, pp. 375-387.

US 8,431,118 B2

ANTI-HERPES SIMPLEX VIRUS ANTIBODIES AND METHODS OF USE THEREOF

CROSS-REFERENCE TO RELATED APPLICATIONS

This application is a divisional of U.S. application Ser. No. 12/651,325, filed on Dec. 31, 2009, which is a continuation-in-part application of U.S. patent application Ser. No. 12/348,550, filed Jan. 5, 2009, which are incorporated herein by reference in their entirety.

BACKGROUND OF THE INVENTION

Herpes simplex virus (HSV) is a member of the herpes virus family, which causes infection in humans. HSV infection results in a number of distinct medical disorders, depending on the infection sites. Infections in the mouth, face, hand, and genitals generally do not cause severe complications. However, infections in the eye, central nervous system, and brain can be life-threatening. Patients with immature or suppressed immune systems, such as newborns, transplant recipients, and HIV carriers, are prone to severe complications from HSV infections.

Several approaches are currently available for treating HSV infection, including antiviral medication and vaccine. However, there is still a need for the development of a drug that prevents or treats HSV infections.

SUMMARY OF THE INVENTION

The present invention is based on the identification of human anti-HSV antibodies that exhibit high efficacy in inhibiting reproduction of HSV. The antibodies of the invention bind to a conformational epitope on the glycoprotein D (gD) of HSV-1 and HSV-2.

In one aspect, the invention provides an isolated antibody (e.g., human antibody) or polypeptide that specifically binds to the gD of herpes simplex virus-1 (HSV-1) and herpes simplex virus-2 (HSV-2), wherein the antibody or the polypeptide binds to a conformational epitope on the glycoprotein D, and the epitope comprises amino acids Y38, D215, P221, and R222 shown in SEQ ID NO:44 or SEQ ID NO:45 or the amino acids on the gD corresponding to amino acids Y38, D215, P221, and R222 shown in SEQ ID NO:44 or SEQ ID NO:45. In some embodiments, the antibody binds to or interacts with amino acids 35-40 and 215-222 shown in SEQ ID NO:44 or SEQ ID NO:45 or the amino acids corresponding to the amino acids 35-40 and 215-222 shown in SEQ ID NO:44 or SEQ ID NO:45 on the gD.

In another aspect, this invention features an antibody that specifically binds to the gD of HSV (e.g., an antibody that specifically binds to the gD of HSV-1 and HSV-2). This antibody contains (1) a heavy chain variable region ($V_H$) and a light chain variable region ($V_L$) including amino acid sequences at least 80% (e.g., at least any of 85%, 90%, 95%, 99%, or 100%) identical to the $V_H$ (SEQ ID NO:1 or amino acids 3-124 of SEQ ID NO:1) and $V_L$ (SEQ ID NO:2 or amino acids 1-108 of SEQ ID NO:2) of single-chain antibody scFv E317, respectively, (2) a $V_H$ and a $V_L$ including amino acid sequences at least 80% (e.g., at least any of 85%, 90%, 95%, 99%, or 100%) identical to the $V_H$ (SEQ ID NO:3 or amino acids 3-124 of SEQ ID NO:3) and $V_L$ (SEQ ID NO:4 or amino acids 1-108 of SEQ ID NO:4) of single-chain antibody scFv E425, or (3) a $V_H$ and a $V_L$ including amino acid sequences at least 80% (e.g., at least any of 85%, 90%, 95%, 99%, or 100%) identical to the $V_H$ (SEQ ID NO:41) and $V_L$ (SEQ ID NO:42) of single-chain antibody scFv Y571, respectively. In one example, the anti-HSV antibody of this invention contains all of the complementarity determining regions (CDRs) of scFv E317, scFv E425, or scFv Y571.

Another aspect of the invention relates to a pharmaceutical composition comprising an antibody (including an antigen-binding fragment thereof) or a polypeptide described herein, and a pharmaceutically acceptable carrier.

Another aspect of the present invention relates to an isolated nucleic acid comprising a nucleotide sequence encoding an antibody, a fragment or a region of the antibody described herein. In some embodiments, the invention provides a nucleic acid encoding any of the above-described $V_H$ and $V_L$ regions. In one example, this nucleic acid includes a nucleotide sequence encoding SEQ ID NO:1, amino acids 3-124 of SEQ ID NO:1, SEQ ID NO:2, amino acids 1-108 of SEQ ID NO:2, SEQ ID NO:3, amino acids 3-124 of SEQ ID NO:3, SEQ ID NO:4, amino acids 1-108 of SEQ ID NO:4, SEQ ID NO:41, or SEQ ID NO:42. Preferably, the nucleic acid includes a nucleotide sequence that encodes both SEQ ID NOs:1 and 2, encodes both amino acids 3-124 of SEQ ID NO:1 and amino acids 1-108 of SEQ ID NO:2, encodes both SEQ ID NOs:3 and 4, encodes both amino acids 3-124 of SEQ ID NO:3 and amino acids 1-108 of SEQ ID NO:4, or encodes both SEQ ID NOs:41 and 42. The invention also provides a vector (such as an expression vector) or a host cell comprising one or more nucleic acids described herein.

The invention also provides methods for producing an antibody or an antigen-binding fragment thereof comprising culturing a host cell described herein that produces the antibody or the fragment, and recovering the antibody or the fragment form the cell culture. Mammalian cells (such as COS, HeLa, and CHO cells) and non-mammalian cells including prokaryotes (such as E. coli) and yeast may be used as host cells for producing the antibodies.

In yet another aspect, this invention features a method for treating or preventing HSV infection by administering to a subject in need thereof an effective amount of either the antibody of this invention or its encoding nucleic acid(s). The antibody or the nucleic acid(s) can also be used for the manufacture of a medicament for treating HSV infection. The term "treating" as used herein refers to the application or administration of a composition including one or more active agents to a subject, who is infected with HSV or at risk for HSV infection, with the purpose to cure, heal, alleviate, relieve, alter, remedy, ameliorate, improve, or affect the infection, the symptoms of the infection, or the predisposition toward the infection. "An effective amount" as used herein refers to the amount of each active agent required to confer therapeutic effect on the subject, either alone or in combination with one or more other active agents. Effective amounts vary, as recognized by those skilled in the art, depending on route of administration, excipient choice, and co-usage with other active agents. The antibody may be administered prior to or after exposure to a HSV (such as HSV-1 or HSV-2).

Also within the scope of this invention is a method of diagnosing HSV infection in a subject with the anti-HSV antibody described above. This method includes (a) contacting the antibody with a biological sample obtained from the subject and suspected of containing HSV viral particles or proteins, and (b) determining an antigen-antibody reaction. Detection of such a reaction indicates presence of HSV in the sample.

The details of one or more embodiments of the invention are set forth in the description below. Other features or advantages of the present invention will be apparent from the following detailed description of several embodiments, and also from the appended claims.

DETAILED DESCRIPTION OF THE INVENTION

Figure 1:
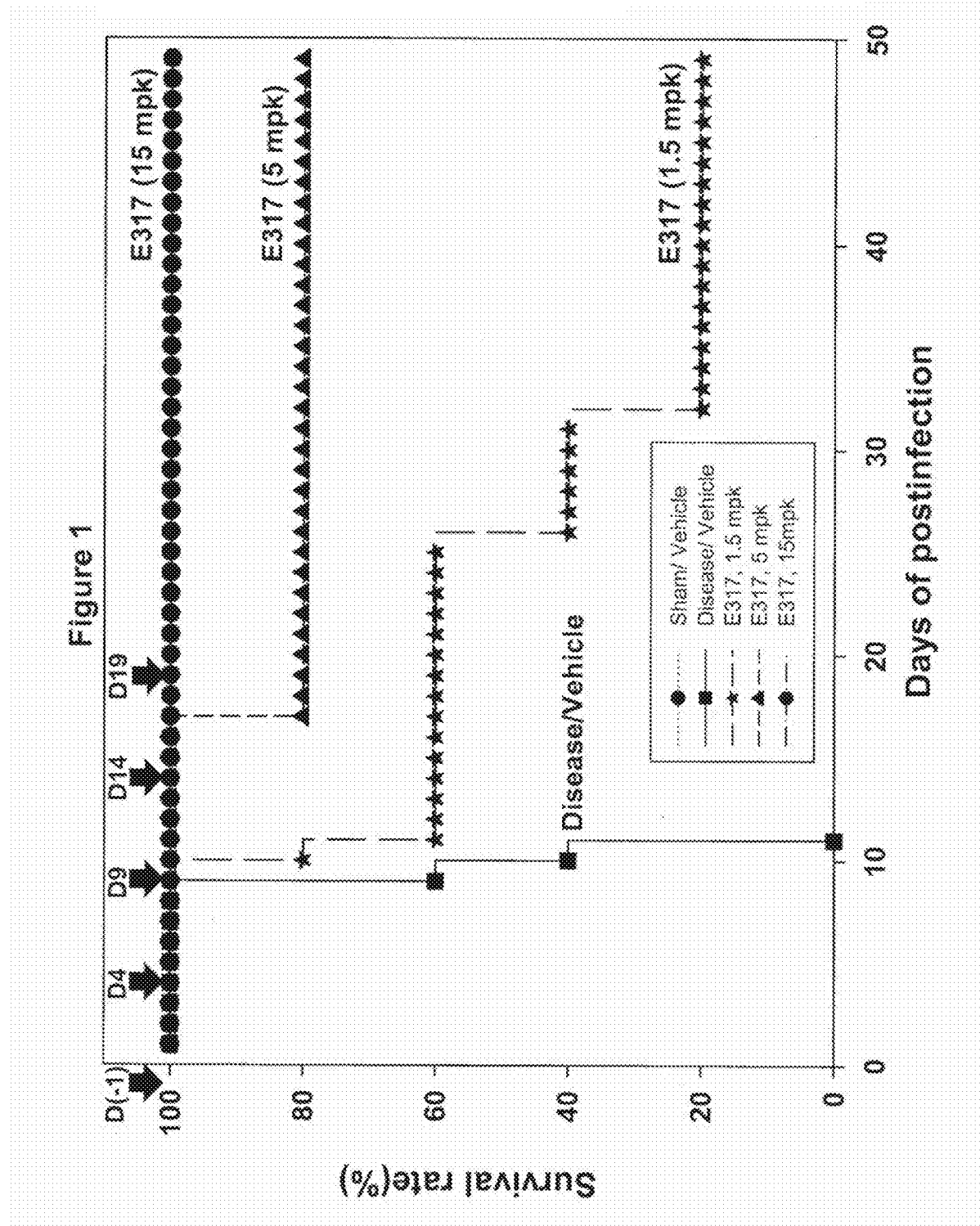
FIG. 1 shows the results on the protection from HSV lethality in HSV1-infected SCID mice by multiple mAb E317 dosage administrations at dosages of 1.5 mpk, 5 mpk, or 15 mpk. mAb E317 was administered five times at a five-day interval starting at 24 hours prior to virus inoculation.

The invention provides antibodies and polypeptides that bind to the glycoprotein D of HSV-1 and HSV-2 and neutralize HSV-1 and HSV-2. These antibodies and polypeptides bind to a non-linear conformational epitope on the gD, wherein the epitope comprises amino acids D215, P221, and R222 shown in SEQ ID NO:44 or SEQ ID NO:45, or the amino acids on the gD corresponding to amino acids D215, P221, and R222 shown in SEQ ID NO:44 or SEQ ID NO:45.

In some embodiments, the epitope further comprises amino acid Y38 or the amino acid on the gD corresponding to Y38 shown in SEQ ID NO:44 or SEQ ID NO:45. In some embodiments, the antibody binds to or interacts with amino acids 35-40 and 215-222 shown in SEQ ID NO:44 or SEQ ID NO:45 or the amino acids on the gD corresponding to the amino acids 35-40 and 215-222 shown in SEQ ID NO:44 or SEQ ID NO:45.

It was generally believed that HSV entry into cells requires the interaction of gD with one of several potential entry receptors: (a) herpes virus entry mediator (HVEM), a member of the TNF receptor family; (b) nectin-1, a member of the immunoglobulin superfamily; and (c) 3-O-sulfated heparan sulphate. See Reske et al., Rev. Med. Virol. 17:205-215, 2007. HSV-1 gD is a type I membrane glycoprotein consisting of 369 amino acids within an N-terminal ectodomain of 316 amino acids. The protein's ectodomain core is of a V-like domain of the immunoglobulin fold (residues 56-184). Within the N-terminal extension to the core, a 37 residue hairpin structure (bending at residue 21) forms the entire site which contacts the receptor HVEM. In the absence of HVEM, the N-terminus adopts an extended and flexible conformation. Without wishing to be bound by theory, the antibodies described herein may bind to amino acids of the gD that interact with the N-terminal sequences when the hairpin structure of the gD is formed, and the binding of the antibody to the gD may prevent the formation of the hairpin structure. It has been demonstrated that antibodies that specifically bind this portion of the gD exhibits high efficacy in inhibiting reproduction of HSV in vitro and in vivo.

The antibodies or polypeptides described herein may have one or more of the following characteristics: (a) specifically bind to the gD of HSV-1 and HSV-2; (b) bind to a non-linear conformation epitope of the gD; (c) bind to an epitope including at least amino acids D215, P221, and R222 shown in SEQ ID NO:44 or SEQ ID NO:45 or the amino acids on the gD corresponding to amino acid residues D215, P221, and R222 shown in SEQ ID NO:44 or SEQ ID NO:45; (d) bind to an epitope including amino acids Y38, D215, P221, and R222 shown in SEQ ID NO:44 or SEQ ID NO:45 or the amino acids on the gD corresponding to amino acid residues Y38, D215, P221, and R222 shown in SEQ ID NO:44 or SEQ ID NO:45; (e) bind to or interact with amino acids 35-40 and 215-222 shown in SEQ ID NO:44 or SEQ ID NO:45 or the amino acids on the gD corresponding to the amino acids 35-40 and 215-222 shown in SEQ ID NO:44 or SEQ ID NO:45; (f) binding of the antibodies or polypeptides to the gD is disulfide bond dependent; (g) do not bind the gD if amino acids 224-240 shown in SEQ ID NO:44 or 45 or amino acids on the gD corresponding to the amino acids shown in SEQ ID NO:44 or 45 are deleted; (h) do not bind to the gD if amino acids 27-43 shown in SEQ ID NO:44 or 45 or amino acids on the gD corresponding to amino acids 27-43 shown in SEQ ID NO:44 or 45 are deleted; (i) having an $IC_{50}$ between about 1 nM to about 10 nM in inhibiting HSV-1 and/or HSV-2 reproduction in a plaque reduction assay; and (j) prevent or treat HSV infection in a subject.

Glycoprotein D of different strains of HSV-1 and HSV-2 may have variations in amino acid sequences. The alignment for the amino acid sequences of the gD from KOS (a strain of HSV-1) (SEQ ID NO:44) and the gD from HG52 (a strain of HSV-2) (SEQ ID NO:45) is shown below. One skilled in the art can easily identify amino acid residues in a glycoprotein D that correspond to the positions shown in SEQ ID NO:44 or 45.

```
                10        20        30        40        50
gD-KOS   KYALADASLKMADPNRFRGKDLPVLDQLTDPPGVRRVYHIQAGLPDPFQP
gD-HG52  KYALADPSLKMADPNRFRGKNLPVLDQLTDPPGVKRVYHIQPSLEDPFQP 60        70        80        90       100
gD-KOS   PSLPITVYYAVLERACRSVLLNAPSEAPQIVRGASEDVRKQPYNLTIAWF
gD-HG52  PSIPITVYYAVLERACRSVLLHAPSEAPQIVRGASDEARKHTYNLTIAWY 110       120       130       140       150
gD-KOS   RMGGNCAIPITVMEYTECSYNKSLGACPIRTQPRWNYYDSFSAVSEDNLG
gD-HG52  RMGDNCAIPITVMEYTECPYNKSLGVCPIRTQPRWSYYDSFSAVSEDNLG 160       170       180       190       200
gD-KOS   FLMHAPAFETAGTYLRLVKINDWTEITQFILEHRAKGSCKYALPLRIPPS
gD-HG52  FLMHAPAFETAGTYLRLVKINDWTEITQFILEHRARASCKYALPLRIPPA 210       220       230       240       250
gD-KOS   ACLSPQAYQQGVTVDSIGMLPRFIPENQRTVAVYSLKIAGWHGPKAPYTS
gD-HG52  ACLTSKAYQQGVTVDSIGMLPRFIPENQRTVALYSLKIAGWHGPKPPYTS 260       270       280       290       300
gD-KOS   TLLPPELSETPNATQPELAPEDPEDSALLEDPVGTVAPQIPPNWHIPSIQ
gD-HG52  TLLPPELSDTTNATQPELVPEDPEDSALLEDPAGTVSSQIPPNWHIPSIQ 310       320       330       340       350
gD-KOS   DAATPYHPPATPNNMGLIAGAVGGSLLAALVICGIVYWMHRRTRKAPKRI
gD-HG52  DVA-PHHAPAAPSNPGLIIGALAGSTLAVLVIGGIAFWVRRRAQMAPKRL 360       370       380       390       400
gD-KOS   RLPHIREDDQPSSHQPLFY (SEQ ID NO: 44)
gD-HG52  RLPHIRDDDAPPSHQPLFY (SEQ ID NO: 45)
```

The term "antibody" is meant to include intact naturally-occurring antibodies and their fragments (e.g., Fab and F(ab')₂) and genetically modified antibodies (e.g., scFv antibodies, chimeric antibodies, diabodies, and dual variable domain immunoglobulins). In some embodiments, the antibody is a human antibody. In some embodiments, the antibody is a humanized antibody.

An "isolated" molecule or material (e.g., an antibody and a nucleic acid) is one which has been identified and separated and/or recovered from a component of its natural environment. In some embodiments, the molecule or material is purified. For example, the material may be at least 90% pure (i.e., free from contaminants), at least 95% pure, or at least 99% pure.

As used herein and in the appended claims, the singular forms "a", "an", and "the" include plural reference unless the context clearly indicates otherwise. It is understood that aspect and variations of the invention described herein include "consisting" and/or "consisting essentially of" aspects and variations.

Also disclosed herein are human antibodies, e.g., E317, E425 and Y571, that specifically bind to both herpes simplex virus 1 (HSV-1) and herpes simplex virus 2 (HSV-2), in particular, their glycoprotein D.

The E317 antibody contains a $V_H$ fragment, which or a portion of which has the amino acid sequence shown in residues 3-124 of SEQ ID NO:1; and a $V_L$ fragment, which or a portion of which has the amino acid sequence shown in residues 1-108 of SEQ ID NO:2. These two amino acid sequences are shown below:

```
Amino acid sequence of the E317 V_H fragment
                                                (SEQ ID NO: 1)
MAQVTLKQSGAEVKKPGSSVKVSCTASGGTLRTYGVSWVRQAPGQGLEWLGRTIPLFGKTDYAQ KFQGRVTITADKSMDTSFMELTSLTSEDTAVYYCARDLTTLTSYNWWDLWGQGTLVTVSS
[* The underlined regions in the above sequence refer to
complementarity-determining regions (CDRs)].

Amino acid sequence of the E317 V_L fragment
                                                (SEQ ID NO: 2)
EIVLTQSPGTLSLSPGERATLSCRASQSVTSSQLAWYQQKPGQAPRLLISGASNRATGIPDRFS GSGSGTDFTLTISRLEPEDFAVYYCQQYGSSPTFGGGTKVEIKRAA
[* The underlined regions in the above sequence refer to CDRs.]
```

The E425 antibody contains a $V_H$ fragment, which or a portion of which has the amino acid sequence shown in residues 3-124 of SEQ ID NO:3 and a $V_L$ fragment, which or a portion of which has the amino acid sequence shown in residues 1-108 of SEQ ID NO:4. Both of the sequences are shown below:

```
Amino acid sequence of the E425 V_H fragment
                                                    (SEQ ID NO: 3)
MAQVQLQQSGAGVKKPGSSVRVSCSASGGTLRTYALSWVRQVPGQGFEWMGRIIPMFGKTDYAQ KFQGRLSITADKSMDTGFMELTSLTSEDTAVYYCARDLTTLTSYNWLDIWGQGTLVTVSS
[* The underlined regions in the above sequence refer to CDRs.]

Amino acid sequence of the E425 V_L fragment
                                                    (SEQ ID NO: 4)
ETTLTQSPGTLSLSPGERATLSCRASQSVSSNYLAWYQKKPGQAPRLLIYGASSRATGIPDRFS GSGSGTDFTLTINRLEPEDFAVYYCQQYGRSPTFGQGTKVEIKRAA
[* The underlined regions in the above sequence refer to CDRs.]
```

The Y571 antibody contains a V_H fragment, which or a portion of which has the amino acid sequence of SEQ ID NO:41 and a V_L fragment, which or a portion of which has the amino acid sequence of SEQ ID NO:42. Both of the sequences are shown below:

```
Amino acid sequence of the Y571 V_H fragment
                                                    (SEQ ID NO: 41)
QVQLQQSGAEVKKPGSSVKVSCKASGGTLRTYGVSWVRQAPGQGLEWLGGTIPLFGKTDYAQKF QGRVTITADKSMDTSFMELTSLTSEDTAVYYCARDLTTLTSYNWWDLWGQGTLVTVSS
[* The underlined regions in the above sequence refer to CDRs.]

Amino acid sequence of the Y571 V_L fragment
                                                    (SEQ ID NO: 42)
ETTLTQSPGILSLSPGDRATLSCRASQSVGSVNLAWYQQRPGQAPRLLIHGASNRATGIPDRFS GVGSGTDFTLTINRLEPDDFAVYYCQQYGTSPITFGQGTRLEIKR
[* The underlined regions in the above sequence refer to CDRs.]
```

The invention also provides antibodies and polypeptides that compete with antibody scFv E317, scFv E425, and/or scFv Y571 for binding to the gD of HSV-1 and/or HSV-2. An antibody or polypeptide is considered competing with another antibody or polypeptide if the binding of one antibody or polypeptide to the gD is significantly inhibited by the presence of the second antibody or polypeptide at increasing concentrations. For example, the inhibition can be at least 50%, at least 60%, at least 70%, at least 80%, or at least 90%. In some embodiments, the antibodies and polypeptides are able to neutralize HSV-1 and HSV-2 with substantially equivalent potency. The potency may be measured in vitro or in vivo. For example, the antibody or polypeptide may have an $IC_{50}$ from about 1 nM to about 10 nM (such as from about 1 nM to about 6 nM, or about 1 nM to about 5 nM) in the plaque assay described in Example 3.

Also disclosed herein are functional equivalents of the E317, E425, and Y571 antibody. Such a functional equivalent is an antibody that specifically binds to HSV glycoprotein D and has a V_H fragment, which or a portion of which is at least 70% (e.g., 75%) identical to SEQ ID NO:1, SEQ ID NO:3, or SEQ ID NO:41, and a V_L fragment, which or a portion of which is at least 70% (e.g., 75%) identical to SEQ ID NO:2, SEQ ID NO:4, or SEQ ID NO:42.

As used herein, "percent homology" of two amino acid sequences is determined using the algorithm described in Karlin and Altschul, *Proc, Natl. Acad. Sci. USA* 87:2264-2268, 1990, modified as described in Karlin and Altschul, *Proc, Natl. Acad. Sci. USA* 5873-5877, 1993. Such an algorithm is incorporated into the NBLAST and XBLAST programs of Altschul et al., *J. Mol. Biol.* 215:403-410, 1990. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al., *Nucleic Acids Res.* 25:3389-3402, 1997. When utilizing the BLAST and Gapped BLAST programs, the default parameters of the respective programs (e.g., XBLAST and NBLAST) are used.

The antibody of this invention can contain only the V_H and V_L fragments of E317, E425, or Y571 described above. It can be a single-chain antibody (scFv), in which the V_H; and V_L fragments are connected either directly or via a linker (e.g., a peptide linker). In one example, the antibody is scFv E317, the amino acid sequence of which is shown below:

```
Amino acid sequence of ScFv E317
                                                       (SEQ ID NO: 5)
QVTLKQSGAEVKKPGSSVKVSCTASGGTLRTYGVSWVRQAPGQGLEWLGRTIPLFGKTDYAQKF

QGRVTITADKSMDTSFMELTSLTSEDTAVYYCARDLTTLTSYNWWDLWGQGTLVTVSSGGGGSG

GGGSGGGGSEIVLTQSPGTLSLSPGERATLSCRASQSVTSSQLAWYQQKPGQAPRLLISGASNR

ATGIPDRFSGSGSGTDFTLTISRLEPEDFAVYYCQQYGSSPTFGGGTKVEIKR
(* The underlined region refers to the peptide linker connecting
the V_H and V_L fragments.)
```

In another example, the antibody is scFv E425, having the amino acid of SEQ ID NO:6 shown below:

```
Amino acid sequence of ScFv E425
                                                       (SEQ ID NO: 6)
QVQLQQSGAGVKKPGSSVRVSCSASGGTLRTYALSWVRQVPGQGFEWMGRIIPMFGKTDYAQKF

QGRLSITADKSMDTGFMELTSLTSEDTAVYYCARDLTTLTSYNWLDIWGQGTLVTVSSGGGGSG

GGGSGGGGSETTLTQSPGTLSLSPGERATLSCRASQSVSSNYLAWYQKKPGQAPRLLIYGASSR

ATGIPDRFSGSGSGTDFTLTINRLEPEDFAVYYCQQYGRSPTFGQGTKVEIKR
(* The underlined region refers to the peptide linker connecting
the V_H and V_L fragments.)
```

In another example, the antibody is scFv Y571, having the amino acid of SEQ ID NO:43 shown below:

```
Amino acid sequence of ScFv Y571
                                                       (SEQ ID NO: 43)
QVQLQQSGAEVKKPGSSVKVSCKASGGTLRTYGVSWVRQAPGQGLEWLGGTIPLFGKTDYAQKF

QGRVTITADKSMDTSFMELTSLTSEDTAVYYCARDLTTLTSYNWWDLWGQGTLVTVSSGGGGSG

GGGSGGGGSETTLTQSPGILSLSPGDRATLSCRASQSVGSVNLAWYQQRPGQAPRLLIHGASNR

ATGIPDRFSGVGSGTDFTLTINRLEPDDFAVYYCQQYGTSPITFGQGTRLEIKR
(* The underlined region refers to the peptide linker connecting
the V_H and V_L fragments.)
```

The invention also provides antibodies or polypeptides comprising a heavy chain variable region comprising one, two, or three CDRs from SEQ ID NO:1 and/or a light chain variable region comprising one, two, or three CDRs from SEQ ID NO:2. The invention also provides antibodies or polypeptides comprising the heavy chain variable region comprising the amino acid residues 3-124 shown in SEQ ID NO:1 and/or the light chain variable region comprising the amino acid residues 1-108 shown in SEQ ID NO:2. The invention also provides antibodies or polypeptides comprising a heavy chain variable region comprising one, two, or three CDRs from SEQ ID NO:3 and/or a light chain variable region comprising one, two, or three CDRs from SEQ ID NO:4. The invention also provides antibodies or polypeptides comprising the heavy chain variable region comprising the amino acid residues 3-124 shown in SEQ ID NO:3 and/or the light chain variable region comprising the amino acid residues 1-108 shown in SEQ ID NO:4. The invention also provides antibodies or polypeptides comprising a heavy chain variable region comprising one, two, or three CDRs from SEQ ID NO:41 and/or a light chain variable region comprising one, two, or three CDRs from SEQ ID NO:42. The invention also provides antibodies or polypeptides comprising the heavy chain variable region comprising the amino acid sequence shown in SEQ ID NO:41 and/or the light chain variable region comprising the amino acid sequence shown in SEQ ID NO:42. The invention also provides antibodies or polypeptides comprising the amino acid sequence shown in SEQ ID NO:5, 6, or 43.

As used herein, a "complementarity determining region" or "CDR" includes a CDR by any definition, such as a Kabat CDR (Kabat et al., Sequences of Proteins of Immunological Interest, 5th Ed. Public Health Service, National Institutes of Health, Bethesda, Md. (1991)), a Chothia CDR (Chothia and Lesk, J. Mol. Biol. 196:901-917 (1987)), and combined CDRs. In some embodiments, the CDR is an abbreviated CDR which includes stretches of CDR residues that include all the specificity determining residues (SDRs) (Kashmiri et al., Methods 36:25-34, 2005). In some embodiments, the invention provides antibodies comprising all the SDRs from antibody ScFv E317, ScFv E425, or ScFv Y571.

The antibody of this invention can also be a whole immunoglobulin molecule, in which the $V_H$ and $V_L$ fragments are respectively linked to a heavy chain constant region and a light chain constant region of an immunoglobulin, e.g., human IgG1, IgG2a, IgG2b, IgG3, IgG4, IgM, IgE, IgD, IgA1, and IgA2.

The antibodies described herein may be generated by screening an antibody library (such as a phage display library) and identify antibodies that have the desired binding properties using methods known in the art and described herein. See, e.g., Examples 1-5.

Any of the above-described antibodies can be made using conventional recombinant technology. For example, the antibody may be produced in a host cell by expressing a nucleic acid encoding the antibody, and recovering the antibody from the cell culture. For example, the E317, E425, or Y571 antibody can be prepared by expressing polypeptides containing residues 3-124 of SEQ ID NO:1, residues 3-124 of SEQ ID NO:3, or SEQ ID NO:41 for the $V_H$, and/or residues 1-108 of SEQ ID NO:2, residues 1-108 of SEQ ID NO:4, or SEQ ID NO:42 for the $V_L$ in host cells from one or two expression cassettes containing the nucleotide sequences coding for the polypeptides. The $V_H$ and $V_L$ fragments can be made as two separate polypeptides and then refolded together to form an antibody. Alternatively, the two fragments are produced as parts of a single polypeptide.

Functional equivalents of E317, E425, or Y571 can be produced by introducing mutations in their $V_H$ and $V_L$ fragments, preferably, in the frame regions (FRs). It is well known that the CDRs of an antibody determine its antigen specificity. Thus, mutations, particularly conservative mutations, in the FRs of E317, E425, or Y571 normally would not affect its binding activity to HSV. The antigen specificity of a functional equivalent thus prepared can be confirmed using methods known in the art, e.g., ELISA, immunoprecipitation, or Western-blot analysis.

Both of the antibodies described herein and their encoding nucleic acids are useful in treating HSV infection or reducing HSV reproduction in a human subject who needs the treatment, such as a patient infected with HSV or a patient having a weakened immune system (e.g., infants at risk for congenital HSV infection, pregnant women, organ transplant recipients, cancer patients, leukemia patients, and HIV carriers).

To practice the treatment mentioned above, any of the antibody of this invention or the encoding nucleic acid(s) can be suspended in a pharmaceutically-acceptable carrier (e.g., physiological saline) to form a pharmaceutical composition and administered via a conventional route. The carrier contained in the pharmaceutical composition must be "acceptable" in the sense that it is compatible with the active ingredient of the composition, and preferably, capable of stabilizing the active ingredient and not deleterious to the subject to be treated. The pharmaceutical composition can be administered orally or by intravenous infusion, or injected or implanted subcutaneously, intramuscularly, intrathecally, intraperitoneally, intrarectally, intravaginally, intranasally, intragastrically, intratracheally, or intrapulmonarily. When the encoding nucleic acid(s) is used, it can be delivered via a live vector, such as *Salmonella*, BCG, adenovirus, poxvirus or vaccinia.

The pharmaceutical composition mentioned above can be formulated into dosage forms based on the intended administration routes utilizing conventional methods. For example, it can be formulated in a capsule, a gel seal, or a tablet for oral administration. Capsules can contain any standard pharmaceutically acceptable materials such as gelatin or cellulose. Tablets can be formulated in accordance with conventional procedures by compressing mixtures of the composition with a solid carrier and a lubricant. Examples of solid carriers include starch and sugar bentonite. The capsules or tablets can further contain a binder (e.g., lactose or mannitol), conventional filler, and tableting agent to form hard shell capsules or tablets.

The pharmaceutical composition can also be formulated into parenteral dosage forms, include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic agent.

Injectable compositions containing either the antibody or its encoding nucleic acid(s) may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

To facilitate delivery, the antibody of this invention or its encoding nucleic acid(s) can be conjugated with a chaperon agent. As used herein, "conjugated" means two entities are associated, preferably with sufficient affinity that the therapeutic benefit of the association between the two entities is realized. Conjugated includes covalent or noncovalent bonding as well as other forms of association, such as entrapment of one entity on or within the other, or of either or both entities on or within a third entity (e.g., a micelle).

The chaperon agent can be a naturally occurring substance, such as a protein (e.g., human serum albumin, low-density lipoprotein, or globulin), carbohydrate (e.g., a dextran, pullulan, chitin, chitosan, inulin, cyclodextrin or hyaluronic acid), or lipid. It can also be a recombinant or synthetic molecule, such as a synthetic polymer, e.g., a synthetic polyamino acid. Examples of polyamino acids include polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, and polyphosphazine.

In one example, the chaperon agent is a micelle, liposome, nanoparticle, or microsphere, in which the oligonucleotide is encapsulated. Methods for preparing such a micelle, liposome, nanoparticle, or microsphere are well known in the art. See, e.g., U.S. Pat. Nos. 5,108,921; 5,354,844; 5,416,016; and 5,527,5285.

In another example, the chaperon agent serves as a substrate for attachment of one or more of a fusogenic or condensing agent.

A fusogenic agent is responsive to the local pH. For instance, upon encountering the pH within an endosome, it can cause a physical change in its immediate environment, e.g., a change in osmotic properties which disrupts or increases the permeability of the endosome membrane, thereby facilitating release of the antibody or nucleic acid(s) into host cell's cytoplasm. A preferred fusogenic agent changes charge, e.g., becomes protonated at a pH lower than a physiological range (e.g., at pH 4.5-6.5). Fusogenic agents can be molecules containing an amino group capable of undergoing a change of charge (e.g., protonation) when exposed to a specific pH range. Such fusogenic agents include polymers having polyamino chains (e.g., polyethyleneimine) and membrane disruptive agents (e.g., mellittin). Other examples include polyhistidine, polyimidazole, polypyridine, polypropyleneimine, and a polyacetal substance (e.g., a cationic polyacetal).

A condensing agent interacts with the antibody/nucleic acid(s), causing it to condense (e.g., reduce the size of the oligonucleotide), thus protecting it against degradation. Preferably, the condensing agent includes a moiety (e.g., a charged moiety) that interacts with the oligonucleotide via, e.g., ionic interactions. Examples of condensing agents include polylysine, spermine, spermidine, polyamine or quarternary salt thereof, pseudopeptide-polyamine, peptidomimetic polyamine, dendrimer polyamine, arginine, amidine, protamine, cationic lipid, cationic porphyrin, and alpha helical peptide.

The dosage of the antibody or the encoding nucleic acid(s) required in the method of this invention depends on the choice of the route of administration; the nature of the formulation; the nature of the subject's illness; the subject's size, weight, surface area, age, and sex; other drugs being administered; and the judgment of the attending physician. Suitable dosages are in the range of 0.01-100.0 mg/kg. Wide variations in the needed dosage are to be expected in view of the variety of compositions available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the composition in a suitable delivery vehicle (e.g., polymeric microparticles or implantable devices) may increase the efficiency of delivery, particularly for oral delivery.

The efficacy of the antibody of this invention for treating HSV infection can be evaluated both in vitro and in vivo. Briefly, the antibody can be tested for its ability to inhibit viral protein production or virus reproduction in vitro. For in vivo studies, the antibody can be injected into an animal (e.g., a mouse model) and its therapeutic effects are then accessed. Based on the results, an appropriate dosage range and administration route can be determined.

Also within the scope of this invention is a method for diagnosing HSV infection in a human subject with the antibody of this invention. In this method, a test sample (e.g., a blood sample or an oral or genital tissue sample) is obtained from a human subject suspected of having HSV infection and then examined for presence of HSV viral proteins using the antibody of this invention via an immunoassays suitable for detecting an antibody-antigen reaction. For example, the test sample can be incubated with an anti-HSV antibody as described herein under conditions suitable for formation of an antibody-antigen complex and the complex, if formed, is detected by a conventional immunoassay, e.g., ELISA, immunoprecipitation, and immunohistochemistry.

The invention also provides kits comprising an antibody or an antigen-binding fragment described herein. In some embodiments, the kits comprise one or more containers comprising the antibody or the fragment described herein and instructions for use in accordance with any of the methods of the invention described herein. In some embodiments, the instructions comprise a description of administration of the antibody or the fragment to prevent or treat HSV infection in a subject. In some embodiments, the instructions comprise a description of using the antibody or the fragment for detecting the presence of HSV in a sample.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference in their entirety.

EXAMPLE 1

Isolation of Human Anti-HSV scFv Antibodies from a Mixed Phage scFv Library

A scFv phage display library was generated using RNAs isolated from 50 healthy Asian adults, following the procedure described in Clackson et al., *Nature*, 352:624-628 (1991). Briefly, mRNAs were purified from B lymphocytes isolated from the 50 healthy Asian adults. cDNAs corresponding to the $V_H$ domains of immunoglobulin proteins were amplified from these mRNAs via RT-PCR, using the following primers:

$V_H$back:

```
HuVH1 abacksfi:
                                    (SEQ ID NO: 7)
5'-GTCCTCGCAACTGCGGCCCAGCCGGCCATGGCCCAGGTGCAGCTG

GTG SARTCTGG-3'

HuVH2abacksfi:
                                    (SEQ ID NO: 8)
5'-GTCCTCGCAACTGCGGCCCAGCCGGCCATGGCCCAGGTCAACTTA

AGGGAGTCTGG-3'

HuVH3abacksfi:
                                    (SEQ ID NO: 9)
5'-GTCCTCGCAACTGCGGCCCAGCCGGCCATGGCCGAGGTGCAGCTG

KTGGAGWCY-3'

HuVH4abacksfi:
                                    (SEQ ID NO: 10)
5'-GTCCTCGCAACTGCGGCCCAGCCGGCCATGGCCCAGGTGCAGCTG

CAGGAGTCSG-3'

HuVH5abacksfi:
                                    (SEQ ID NO: 11)
5'-GTCCTCGCAACTGCGGCCCAGCCGGCCATGGCCGAGGTGCAGCTG

TTGCAGTCTGC-3'

HuVH6abacksfi:
                                    (SEQ ID NO: 12)
5'-GTCCTCGCAACTGCGGCCCAGCCGGCCATGGCCCAGGTACAGCTG

CAGCAGTCA-3'

HuVH14abacksfi:
                                    (SEQ ID NO: 13)
5'-GTCCTCGCAACTGCGGCCCAGCCGGCCATGGCCCAGRTCACCTT

GAAGGAGTCTG-3'

HuVH16abacksfi:
                                    (SEQ ID NO: 14)
5'-GTCCTCGCAACTGCGGCCCAGCCGGCCATGGCCCAGGTGCAGCT

ACAGCAGTGGG-3'
```

$J_K$for:

```
    HuJH1-2for:
                                    (SEQ ID NO: 15)
    5'-TGAGGAGACGGTGACCAGGGTGCC-3'

HuJH3 for:
                                    (SEQ ID NO: 16)
    5'-TGAAGAGACGGTGACCATTGTCCC-3'

HuJH4-5 for:
                                    (SEQ ID NO: 17)
    5'-TGAGGAGACGGTGACCAGGGTTCC-3'

HuJH6 for:
                                    (SEQ ID NO: 18)
    5'-TGAGGAGACGGTGACCGTGGTCCC-3'
``` cDNAs corresponding to the $V_L$ domains of immunoglobulins were amplified using the primers shown below.

$V_K$ back:

HuVK1a back:
(SEQ ID NO: 19)
5'-GACATCCAGATGACCCAGTCTCC-3'

HuVK2a back:
(SEQ ID NO: 20)
5'-GATGTTGTGATGACTCAGTCTCC-3'

HuVK3a back":
(SEQ ID NO: 21)
5'-GAAATTGTGTTGACGCAGTCTCC-3'

HuVK4a back:
(SEQ ID NO: 22)
5'-GACATCGTGATGACCCAGTCTCC-3'

HuVK5a back:
(SEQ ID NO: 23)
5'-GAAACGACACTCACGCAGTCTCC-3'

HuVK6a back:
(SEQ ID NO: 24)
5'-GAAATTGTGCTGACTCAGTCTCC-3'

$J_K$ for Not:

HuJK1 forNot:
(SEQ ID NO: 25)
5'-GAGTCATTCTCGACTTGCGGCCGCACGTTTGATTTCCACCTTGGTCC-3'

HuJK2forNot:
(SEQ ID NO: 26)
5'-GAGTCATTCTCGACTTGCGGCCGCACGTTTGATCTCCAGCTTGGTCC-3'

HuJK3forNot:
(SEQ ID NO: 27)
5'-GAGTCATTCTCGACTTGCGGCCGCACGTTTGATATCCACTTTGGTCC-3'

HuJK4forNot:
(SEQ ID NO: 28)
5'-GAGTCATTCTCGACTTGCGGCCGCACGTTTGATCTCCACCTTGGTCC-3'

HuJK5forNot:
(SEQ ID NO: 29)
5'-GAGTCATTCTCGACTTGCGGCCGCACGTTTAATCTCCAGTCGTGTCC-3'

$V_\lambda$ back:

HuVL1 back:
(SEQ ID NO: 30)
5'-CAGTCTGTGTTGACGCAGCCGCC-3'

HuVL2 back:
(SEQ ID NO: 31)
5'-CAGTCTGCCCTGACTCAGCCTGC-3'

HuVL3a back:
(SEQ ID NO: 32)
5'-TCCTATGTGCTGACTCAGCCACC-3'

HuVL3b back:
(SEQ ID NO: 33)
5'-TCTTCTGAGCTGACTCAGGACCC-3'

HuVL4 back:
(SEQ ID NO: 34)
5'-CACGTTATACTGACTCAACCGCC-3'

HuVL5 back:
(SEQ ID NO: 35)
5'-CAGGCTGTGCTCACTCAGCCGTC-3'

HuVL6 back:
(SEQ ID NO: 36)
5'-AATTTTATGCTGACTCAGCCCCA-3'

$J_\lambda$ for Not:

HuJL1forNot:
(SEQ ID NO: 37)
5'-GAGTCATTCTCGACTTGCGGCCGCACCTAGGACGGTGACCTTGGTCCC-3'

HuJL2-3forNot:
(SEQ ID NO: 38)
5'-GAGTCATTCTCGACTTGCGGCCGCACCTAGGACGGTCAGCTTGGTCCC-3'

HuJL4-5forNot:
(SEQ ID NO: 39)
5'-GAGTCATTCTCGACTTGCGGCCGCACCTAAAACGGTGAGCTGGGTCCC-3'

The $V_H$ cDNAs were randomly linked by PCR reactions with the $V_L$ cDNAs via a linker having the nucleotide sequence of 5'-GGTGGAGGCGGTTCAGGCGGAGGTG-GCTCT GGCGGTGGCGGATCG-3' (SEQ ID NO:40) to form fragments encoding scFv antibodies. These fragments were cloned into pCANTAB 5E phagemid vector to produce the scFv phage display library.

Three additional scFv phage display libraries were constructed using mRNAs isolated from B lymphocytes of an Indian patient, B lymphocytes of a patient having severe acute respiratory syndrome, and spleen cells of a Taiwanese patient, following the procedures described above. These three libraries were combined with the library described above to form a mixed scFv phage display library, which was used to screen for anti-HCMV scFv antibodies. This mixed library, having a phage titer of $1 \times 10^{13}$ pfu/ml, was subjected to screening for clones that express scFv antibodies specific to HSV as follows.

First, phages displaying anti-HSV antibodies were enriched by five rounds of bio-panning as described below. An immunotube was coated with HSV-1 virons diluted in a coating buffer (50 mM sodium bicarbonate, PH9.6, $5 \times 10^5$/ml) at 4° C. overnight, washed three times with PBS containing 0.1% Tween, blocked with PBS containing 2% non-fat milk, and again washed three times with PBS containing 0.1% Tween. An aliquot of the mixed phage library was diluted in PBS containing 2% non-fat milk, and added to the immunotube coated with HSV-1. After a two-hour incubation, the immunotube was washed 10 times with PBS containing 0.1% Tween and then 10 times with PBS to remove unbound phages. The bound phages were eluted using 100 mM triethylaine, neutralized with 1M Tris, PH7.4, and used to infect TG1 bacteria at 37° C. for 30 minutes. The phage-infected TG1 cells were then placed on a plate containing 2×YT medium supplemented with amplicillin and glucose (2YT/amplicillin/glucose medium) and grew at 30° C. overnight. A 2YT/amplicillin/glucose medium supplemented with glycerol was added on the plate and the TG1 cells were dispersed into the medium using a glass spreader. The TG1 cells thus collected were inoculated into a 2YT/amplicillin/glucose medium and cultured at 37° C., 250 rpm until the $OD_{600}$ value of the TG1 culture reached 0.5. After mixing with 5×10¹⁰ pfu of M13KO7 helper phages, the TG1 culture was incubated at 37° C. for 30 minutes and centrifuged at 2,000×g for 10 minutes afterwards at room temperature. The cell pellet thus formed was re-suspended in 10 ml 2×YT medium supplemented with amplicillin and kanamycin and incubated at 30° C., 250 rpm overnight. The culture was centrifuged at 10,000 g for 20 minutes at 4° C. to collect the resultant supernatant. PEG/NaCl was then added to the supernatant. An hour later, the supernatant was centrifuged to collect a pellet containing phage particles. The pellet was re-suspend in PBS and centrifuged to remove the remaining bacterial debris. The phage particles thus collected were again suspended in PBS to form the 1$^{st}$ round scFv phage library enriched in clones expressing anti-HSV antibodies.

An aliquot of this 1$^{st}$ round enriched library was subjected to additional four rounds of biopanning, following the procedures described above, to produce a phage library further enriched in phage clones expressing anti-HSV antibodies. This phage library was subjected to ELISA screening following the process described below to identify individual phage clones expressing anti-HSV single-chain antibodies.

An aliquot of the phage library was diluted and plated on 2×YT medium supplemented with ampilicillin and glucose and incubated at 37° C. overnight. 376 single colonies were picked and incubated separately in 2×YT medium supplemented with ampicillin and glucose at 37° C., 250 rpm overnight. An aliquot of each of the cultures thus obtained was inoculated into a fresh 2×YT medium supplemented with ampicillin and glucose and then mixed with 10⁹ pfu M13KO7helper phage. The mixtures were cultured at 37° C., 250 rpm for 1-2 hours, and then centrifuged at 14,000 rpm for 5 minutes at room temperature. The cell pellets, suspended in 2×YT medium supplemented with ampicillin and kanamycin, were incubated at 30° C., 250 rpm overnight, and then centrifuged at 2000 g for 30 minutes at room temperature. The supernatants were subjected to the ELISA screening as follows.

A test multi-well microplate was coated with lysates of TG1 cells infected with HSV-1 and a control microplate was coated with lysates of *E. coli* cells transfected with vector pET-22b. The supernatants, each containing particles of one of the 376 phage clones mentioned above, were added to the test and control microplates. Both microplates were incubated at room temperature for 2 hours and washed three times with PBS containing 0.05% Tween. HRP-conjugated anti-M13 antibodies, diluted in PBS containing 0.05% Tween and 2% non-fat milk, were then added to both microplates. The plates were incubated at room temperature for 1 hour, washed three times with PBS containing 0.05% Tween, and HRP substrates were added to the microplates. The plates were then incubated at room temperature until a blue color was developed. OD$_{450}$ and OD$_{650}$ values of each well were determined using an ELISA reader.

71 phage clones were found positive (HSV/control>8) in the ELISA screening assay described above. cDNAs encoding the scFv expressed in these clones were amplified and their nucleotide sequences were determined. One of the positive phage clones expresses scFv E317 (SEQ ID NO:5) and another expresses scFv E425 (SEQ ID NO:6). Phage clone expresses scFv Y571 was also isolated.

EXAMPLE 2

Preparation of scFv E317, E425 and Y571

The cDNAs encoding scFv E317, E425, and Y571 were cloned into pET27b(+) expression vector and introduced into *E. coli* for expression. An *E. coli* clone carrying the cDNA encoding scFv E317, scFv E425, or scFv Y571 was incubated overnight at 37° C. in Luria-Bertani (LB) medium supplemented with kanamycin. 70 ml of the overnight culture were inoculated into a fresh LB/kanamycin medium and cultured for 2 hours at 37° C. Isopropyl (β-D-1-thiogalactopyranoside (IPTG) was then added to the culture to a final concentration of 1 mM and the culture was further incubated at 30° C. for 5 hours. *E. coli* cells were harvested via centrifugation, resuspended in Buffer A (50 mM sodium phosphate, 1M sodium chloride, PH8.0), lysated by a microfludizer, and centrifuged again at 14,000 rpm for 20 minutes at 4° C. to obtain a supernatant containing scFv E317, scFv E425, or scFv Y571, which is fused with a His-tag. The His-scFv fusion proteins were purified via affinity column chromatography following conventional procedures. The purified proteins were examined by polyacrylamide gel electrophoresis for purity and quantity.

The antigen-specificity of scFv E317 and scFv E425 was examined by an immunoprecipitation assay described below. 293T cells (2×10⁵) were transfected with 4 µg pLPCX-KOS-gD for expression of HSV glycoprotein D. After being cultured under suitable conditions for 48 hours, the transfected cells were harvested and lyzed using a lysis buffer containing PBS, 1% NP40, 1 mM PMSF, and protease inhibitors. 2 µg His-scFv E317 or His-scFv E425 was incubated with His-tag beads for one hour. After being washed with a phosphate buffer, the His-tag beads were collected and incubated with 10 µl of the cell lysate for one hour. The beads were then washed for several times with RIPA buffer containing 5 mM EDTA and 1% Sodium Deoxycholate; proteins attached to the His-tag beads were eluted and subjected to western-blot analysis, using a commercially available anti-HSV glycoprotein D antibody (1:20000). Results thus obtained indicate that both scFv-317 and scFv-425 bound to HSV glycoprotein D. Using similar experiment, scFv Y571 was shown to bind to HSV glycoprotein D.

EXAMPLE 3

Inhibition of HSV Reproduction with scFv E317 and scFv E425

Plaque reduction assay was employed to examine the ability of scFv E317 and scFv E425 for inhibiting reproduction of HSV-1 and HSV-2. Briefly, 1×10⁵ Vero cells were seeded in each well of a 12-well plate and cultured in MEM medium at 37° C. overnight. The medium was then replaced with a mixture (1 ml/well) containing 1×PBS, MEM (FBS free), HSV-1 KOS, HSV-1 00410 (a clinical strain), HSV-2 186, or HSV-2 00040 (a clinical strain) (5×10² pfu/ml for each virus strain), and one of the antibodies scFv E317 and scFv E425. Before placing in the plate, the mixture was pre-cultured at 37° C. for one hour. An scFv E102 was used as a negative control. The Vero cells were incubated with the mixture at 37° C. for 2 hr and the mixture was then removed. After being washed once with 1×PBS, the plate containing the Vero cells was added with MEM containing 0.4% agarose and 10% FBS. After the agarose was solidified, the plate was placed in a 37° C. incubator for 7 days. During this period, 500 µl MEM containing 10% FBS were added to each well in the plate. At day 8, the medium was removed from each well in the plate, and 500 µl 1×PBS/methanol (1:1 by volume) was then added. Five minutes later, the 1×PBS/methanol was replaced with 500 µl 100% methanol to fix the cells contained in the wells. After another 5 min, the methanol was removed and the cells were stained with 250 µl crystal violet for 10 min. The crystal violet was then washed with water from the plate and the plate was air dried. The numbers of plaques contained in each well in the plate were then counted under a microscope.

The results obtained from the study describe above indicate that scFv E317, E425, and Y571 significantly inhibited plaque formation in Vero cells infected with either HSV-1 or HSV-2. The inhibitory effect of scFv E317, scFv E425, and scFv Y571 is summarized in Tables 1-3 below.

TABLE 1

Inhibitory Effect of scFv E317 on HSV-1 and HSV-2

| | scFv E317 | | | |
|---|---|---|---|---|
| | HSV-1 KOS | HSV-1 00410* | HSV-2 186 | HSV-2 00040* |
| $IC_{50}$ | 5.65 nM | 4.5 nM | 3.6 nM | 1.39 nM |

(*Clinical strains)

TABLE 2

Inhibitory Effect of scFv E425 on HSV-1 and HSV-2

| | scFv E425 | | | |
|---|---|---|---|---|
| | HSV-1 KOS | HSV-1 00410* | HSV-2 186 | HSV-2 00040* |
| $IC_{50}$ | 2.2 nM | 1.8 nM | 4.5 nM | 1.16 nM |

(*Clinical strains)

TABLE 3

Inhibitory Effect of scFv Y571 on HSV-1 and HSV-2

| | scFv YSV1 | |
|---|---|---|
| | HSV-1 KOS | HSV-2 186 |
| $IC_{50}$ | 2.39 nM | 2.12 nM |

In Tables 1-3, $IC_{50}$ refers to the concentration of scFv E317, scFv E425, or scFv Y571 required to reach 50% inhibition on plaque formation in Vero cells infected with HSV. The percentage of inhibition is calculated following the formula below:

% inhibition=100−(plaque number in HSV-infected cells in the presence of antibody)/(plaque number in HSV-infected cells in the absence of antibody)

Control antibody scFv E102 failed to suppress plaque formation in Vero cells infected with either HSV-1 or HSV-2.

EXAMPLE 4

Protection from HSV Lethality In Vivo

In vivo protection studies from HSV-1 by mAb E317 was performed by treating mice inoculated with HSV-1 with antibody mAb E317-103 through intraperitoneal injection, followed by examining the survival rates of the infected mice. In particular, the studies were performed to analyze the effects of mAb E317 dosages and the effects of different mAb E317 dosing schedule (multiple doses versus single dose) on protection from HSV-1. The mouse strain used for these studies was C.B-17 SCID mouse. mAb E317-103 used in these studies is a full length antibody comprising two heavy chains and two light chains. The heavy and light variable regions of mAb E317-103 are from antibody scFv E317, the heavy chain constant region is from human IgG1 heavy chain, and the light chain constant region is from human kappa light chain.

Effect of Multiple Dose Administration of mAb E317-103 on Protection from HSV-1:

Seven-week old male mice were used in this experiment. HSV-1 (KOS) was used to inoculate mice through intraperitoneal administration at the titer of 5×103 PFU. The mice were inoculated with HSV-1 virus on Day 0 (D0). mAb E317-103 was administered to mice through intraperitoneal injection every five days, i.e., it was administered at 24 hours prior to the virus inoculation (Day (−1) or D(−1)), 4 days after inoculation (D4), 9 days after inoculation (D9), 14 days after inoculation (D14), and 19 days after inoculation (D19). The study was performed using different mAb E317-103 dosages: 1.5 milligram antibody per kilogram of mouse body weight (mpk), 5 mpk, or 15 mpk. Two control groups were used, one receiving only phosphate buffer (PBS) ("Sham/Vehicle") and the other receiving only HSV-1 virus ("Disease/Vehicle"). There were 4 animals in Sham/Vehicle control group. There were 5 animals in Disease/Vehicle group and in each of the groups where antibody was administered. The survival rates were monitored daily for seven weeks after mice were inoculated with HSV-1.

The results showed that administration of mAb E317-103 improved the survival of infected mice significantly (FIG. 1). All the mice in the Disease/Vehicle group died within 11 days of post-infection. The survival rates correlate positively with the mAb E317-103 dosage administered, with 100% survival rate for the mice receiving 15 mpk of the antibody, 80% survival rate for the mice receiving 5 mpk of the antibody, and 20% survival rate for the mice receiving 1.5 mpk of the antibody measured 7 weeks of post-infection.

Effect of Single Dose Administration of mAb E317-103 on Protection from HSV-1:

Six-week old male mice were used in this study. HSV-1 (KOS) was used to inoculate mice through intraperitoneal administration at the titer of $5 \times 10^3$ PFU. The mice were inoculated with HSV-1 virus on Day 0 (D0). A single dose of mAb E317-103 was administered to mice at 24 hours prior to the virus inoculation (D(−1)). Different mAb E317-103 dosages were used: 1.5 mpk, 5 mpk, or 15 mpk. Two control groups were used, one receiving only PBS ("Sham/Vehicle") and the other receiving only HSV-1 virus ("Disease/Vehicle"). There were 5 animals in the Sham/Vehicle control group. There were 10 animals in the Disease/Vehicle control group and in each of the groups where antibody was administered. The survival rates were monitored daily for seven weeks after mice were inoculated with HSV-1.

Figure 2:
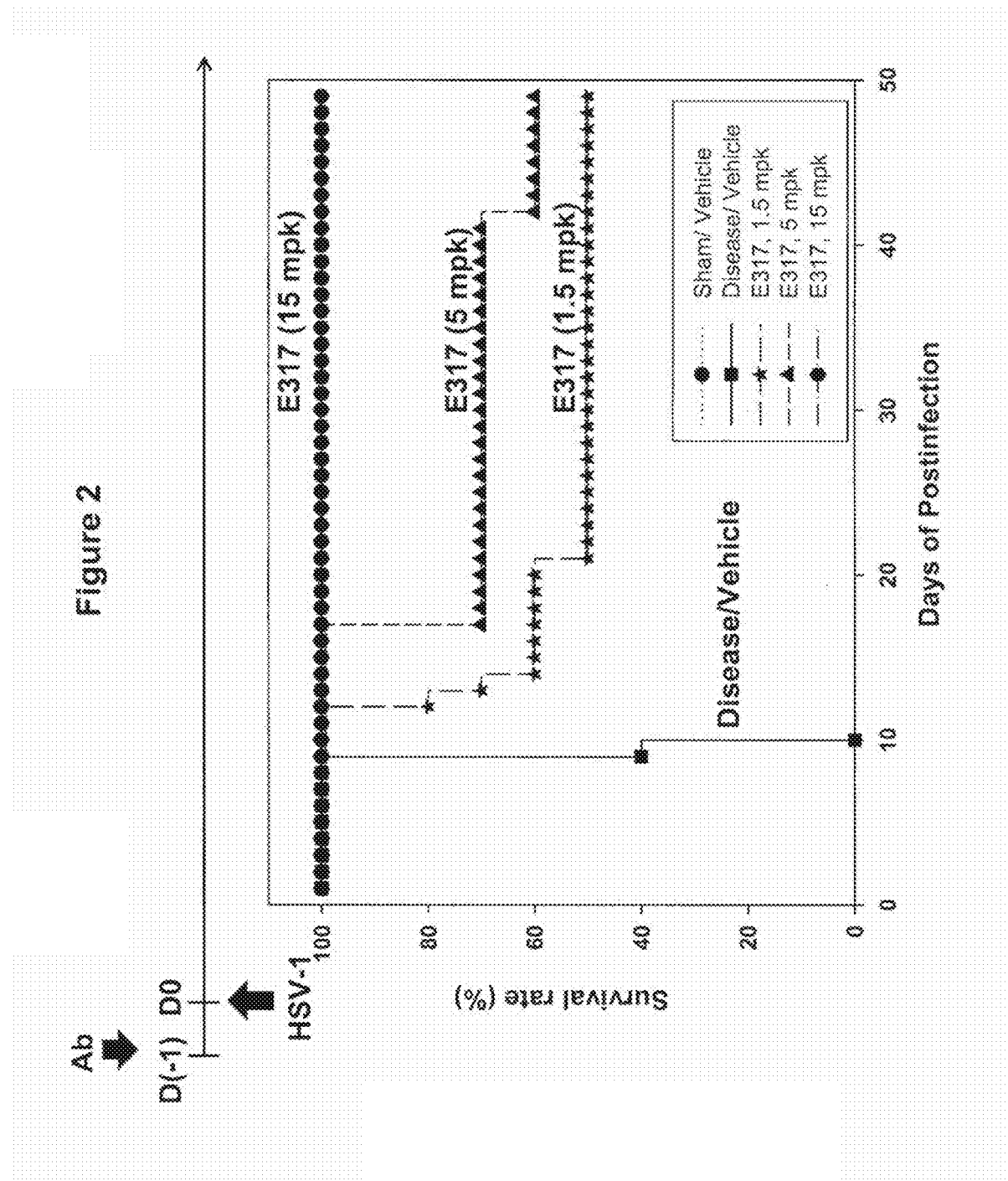
FIG. 2 shows the results on the protection from HSV lethality in HSV1-infected SCID mice by a single mAb E317 injection at the dosage of 1.5 mpk, 5 mpk, or 15 mpk. mAb E317 was administered at 24 hours prior to virus inoculation.

The results showed that, a single dose of mAb E317 was sufficient to provide protection from HSV-1 (FIG. 2). All the mice in the Disease/Vehicle group died within 10 days of post-infection. The survival rates correlate positively with the dosing of mAb E317, with 100% survival rate for the mice receiving 15 mpk of the antibody, 60% survival rate for the mice receiving 5 mpk of the antibody, and 50% survival rate for the mice receiving 1.5 mpk of the antibody about 7 weeks of post-infection. Therefore, a single dose administration of mAb E317 is effective in providing protection from HSV-1.

Effect of Timing of mAb E317-103 Administration on Protection from HSV:

Study was performed to analyze whether antibody was needed prior to virus challenge in order to be protective, or if the antibody could be administered on the same day or even after infection is established. Six-week old male mice were used in this study. HSV-1 (KOS) was used to inoculate mice through intraperitoneal administration at the titer of $5 \times 10^3$ PFU. The day mice were inoculated with HSV-1 virus was considered Day 0 (D0). mAb E317-103 was administered to mice at a single dosage of 15 mpk at 24 hours prior to the virus inoculation (D(−1)), on the same day of the virus inoculation (D0), or 24 hours after the virus inoculation (D1). For D0, virus was injected first and the antibody was injected right after; and the interval between the virus injection and the antibody injection was about 1 min. Two control groups were used, one receiving only PBS ("Sham/Vehicle") and the other receiving only HSV-1 virus ("Disease/Vehicle"). There were 5 animals in the Sham/Vehicle control group. There were 10 animals in the Disease/Vehicle control group and in each of the groups where antibody was administered. The survival rates were monitored daily for at least nine weeks after mice were inoculated with HSV-1.

Figure 3:
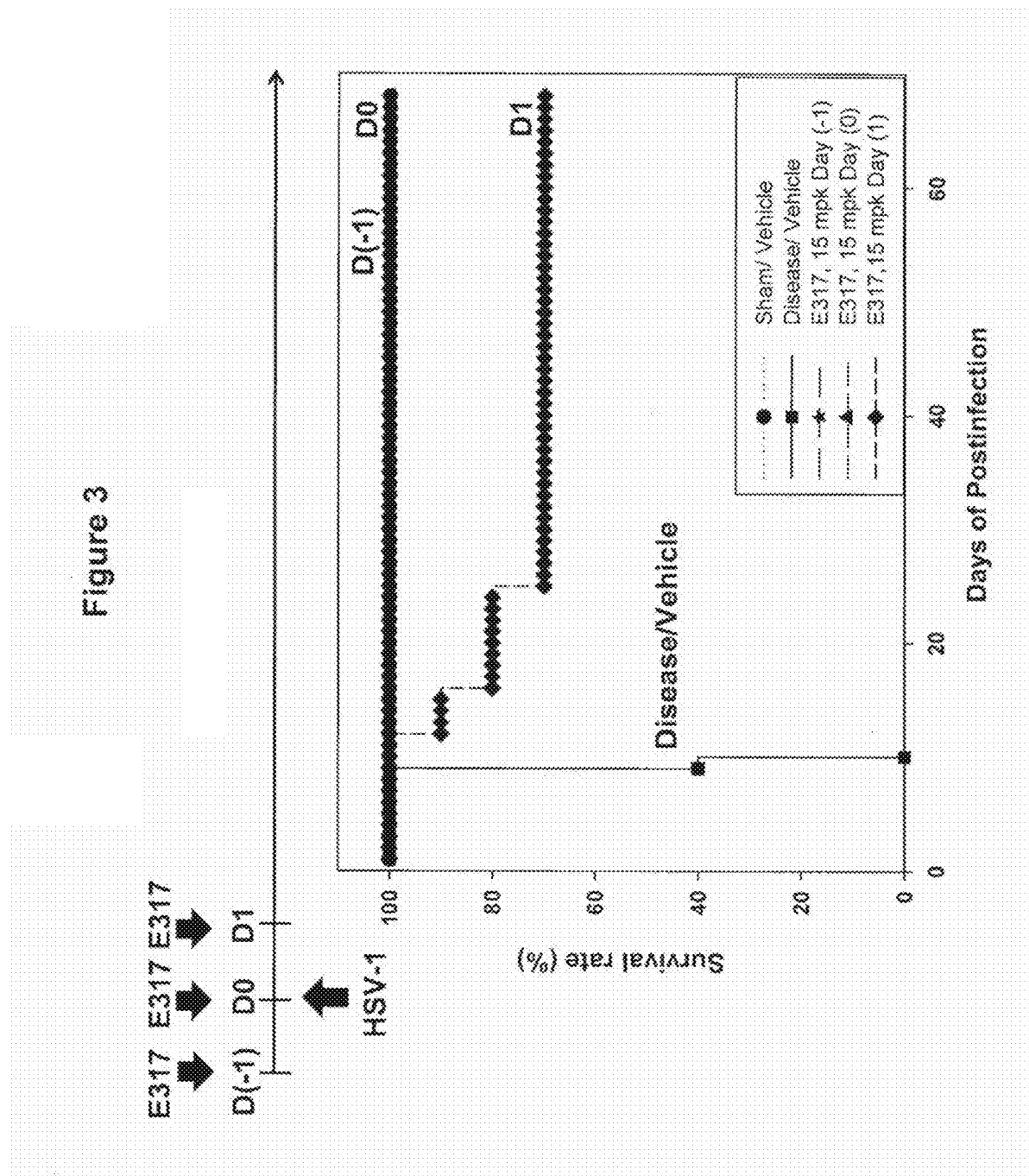
FIG. 3 shows the results on the protection from HSV lethality in HSV1-infected SCID mice by a single mAb E317 injection at 15 mpk at 24 hours prior to virus inoculation, on the same day as virus inoculation, or 24 hours after virus inoculation.

The results showed that administering mAb E317-103 at 24 hours prior to virus inoculation (D(−1)) and on the same day of inoculation (D0) provided complete protection (100% survival rate for about nine weeks of post-infection) while administering mAb E317-103 at 24 hours post virus inoculation (D1) provided strong protection (70% survival rate for about nine weeks of post-infection) (FIG. 3). Therefore, mAb 317-103 was protective when it was administered prior to infection or post-infection.

EXAMPLE 5

Characterization of the Glycoprotein D Epitope Recognized by mAb E317 and mAb E425

Binding of mAb E317 and E425 to the gD is Conformation Dependent:

The immunoprecipitation assay was performed to determine whether the glycoprotein ("gD") epitope by mAb E317 or E425 is conformation dependent. The assay was performed using existing methods known to one skilled in the art. Briefly, 293T cells were transfected with HSV-1 gD recombinant DNA (from KOS strain) expression construct and cells were harvested after 48 hours. The expression construction was generated by subcloning the cDNA encoding gD into pLPCX (Clontech) digested with XhoI and NotI sites inframe. Cells were lysed in buffer containing PBS, 1% NP40, protease inhibitor, and 1 mM PMSF on ice for 10 minutes. Cell lysates were collected after centrifugation and incubated with HIS-tagged scFv E317 or E425 and HIS-select Nickel Affinity Gel beads (Sigma) in PBS at 4° C. Beads were collected and washed with RIPA buffer (50 mM Tris HCl pH7.4, 150 mM NaCl, 2 mM EDTA, 1% NP-40, 0.1% SDS) six times. The washed beads were analyzed by 12% SDS-PAGE gel or Western Blot using mAb E317 or mAb E425. For the cell lysates immunoprecipitated by mAb E317, gD was shown on SDS-PAGE gel when the proteins on the gel was stained but not on the Western blot using mAb E317 or E425 for immunoblotting. That indicates that the mAb E317 or E425 was not able to bind denatured gD on the Western blot, and the gD epitope recognized by mAb E317 or E425 is not a linear epitope but is conformation dependent.

Mapping the gD Epitope Recognized by mAb E317 or E425:

The gD epitope recognized by mAb E317 was mapped by examining the binding between mutated gD and mAb E317 or E425 through immunoprecipitation assays. The immunoprecipitation assay was performed using existing methods known to one skilled in the art. Briefly, 293T cells were transfected with HSV-1 gD recombinant DNA (from KOS strain) expression construct and cells were harvested after 48 hours. Cells were lysed in buffer containing PBS, 1% NP40, protease inhibitor, and 1 mM PMSF on ice for 10 minutes. Cell lysates were collected after centrifugation and incubated with HIS-tagged scFv E317 and HIS-select Nickel Affinity Gel beads in PBS at 4° C. Beads were collected and washed with RIPA buffer six times. The washed beads were analyzed by performing Western Blot using a commercial anti-HSV gD monoclonal antibody H170 (ViruSys, Cat. No. P1103) as the blotting antibody.

Figure 4:
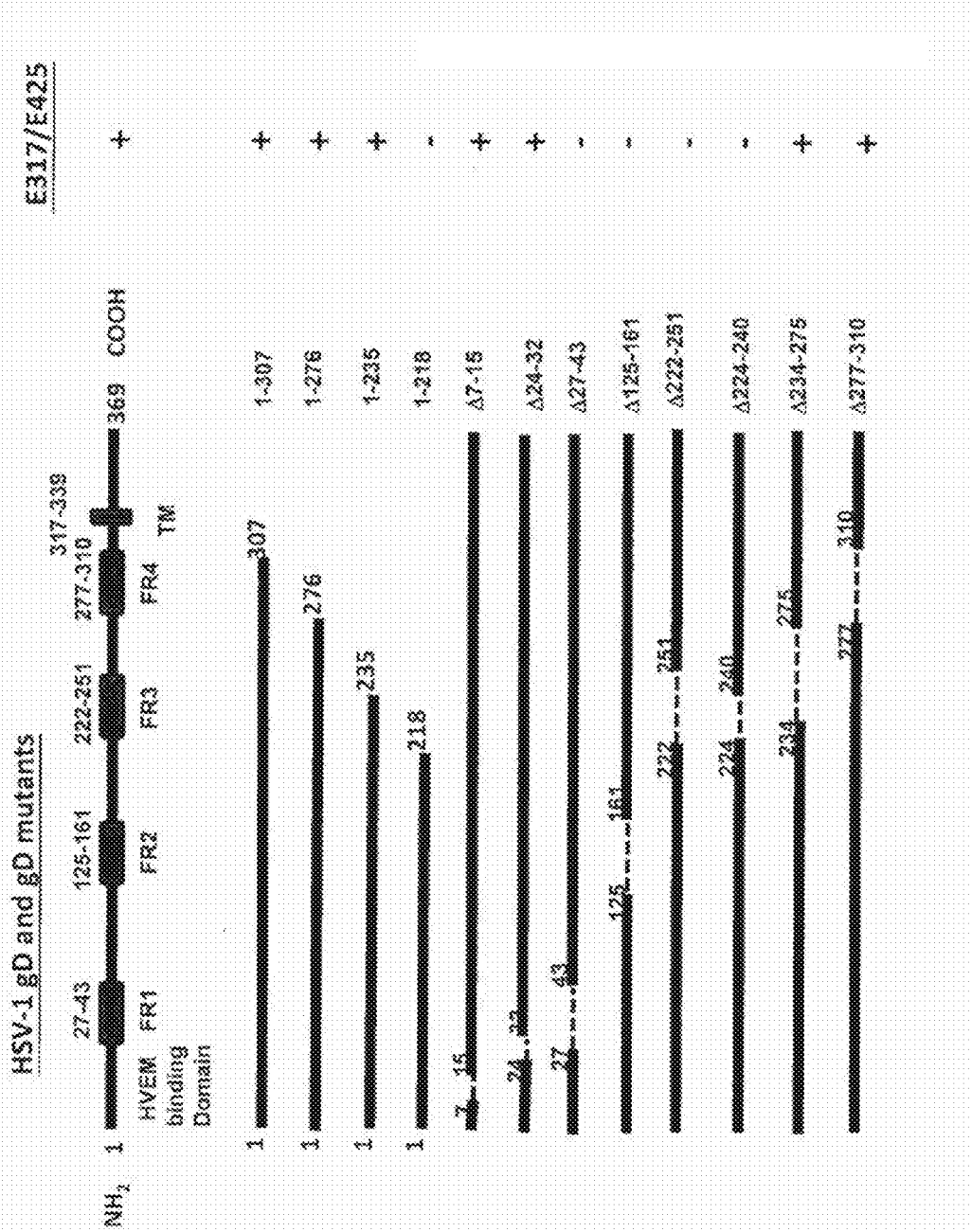
FIG. 4 shows the results of the identification of the regions in glycoprotein D ("gD") important for epitope recognition by mAb E317 through immunoprecipitation assays. "+" indicates that binding of the antibody to the mutant gD was detected; "−" indicates that binding of the antibody to the mutant gD was not detected.
Figure 5:
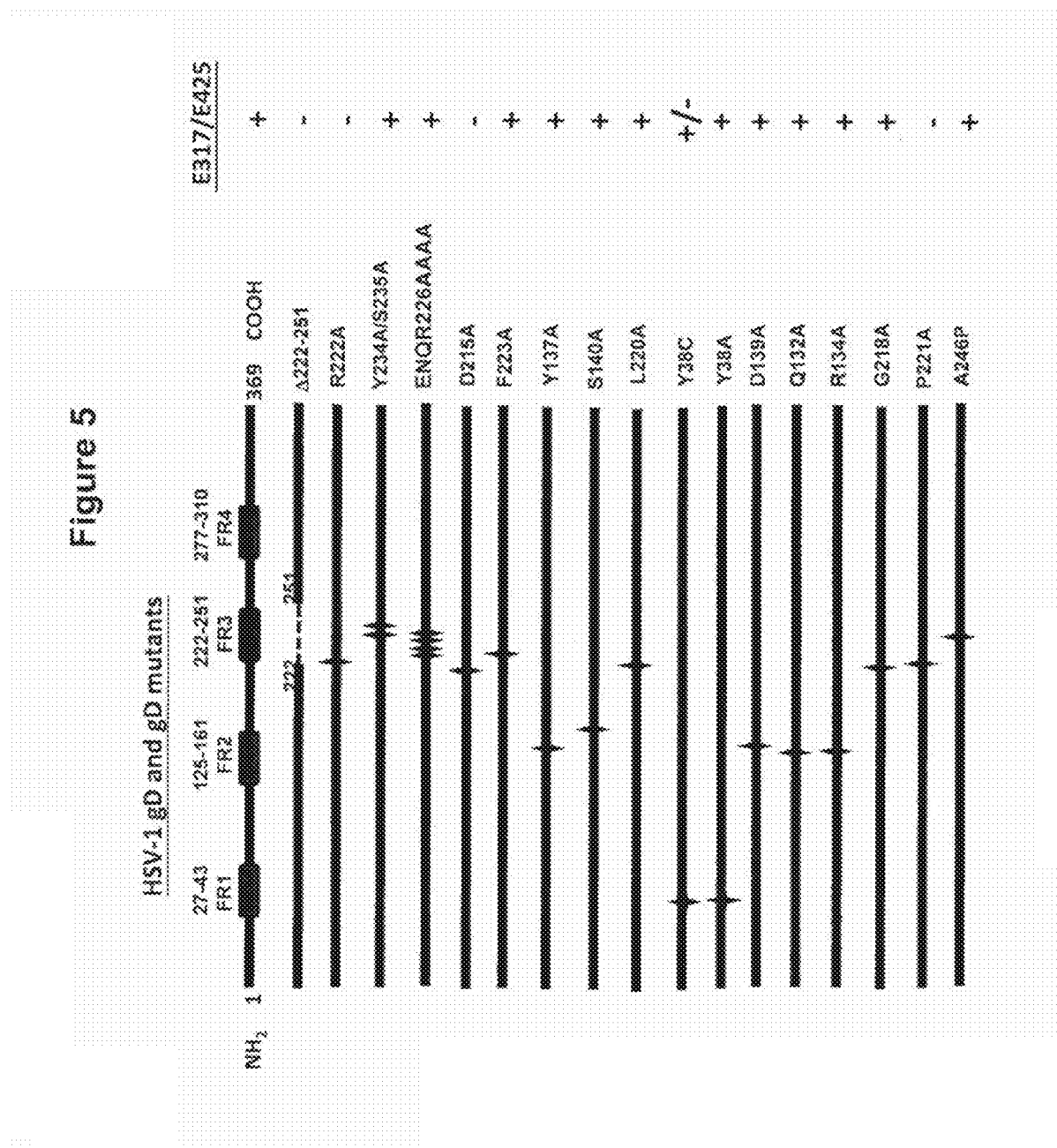
FIG. 5 shows the results of the identification of the amino acids in glycoprotein D ("gD") important for epitope recognition by mAb E317 through immunoprecipitation assays. "+" indicates that binding of the antibody to the mutant gD was detected; "−" indicates that binding of the antibody to the mutant gD was not detected.

HSV-1 gD mutants were generated by methods known to one skilled in the art. Study using truncated gD mutants showed that several regions in gD are important for antibody recognition (FIG. 4). Amino acids 218-235 seem to be important for antibody recognition since binding is shown for gD 1-235 but not for gD 1-218 or gD having deletion of amino acids 224-240. Amino acids 32-43 seem to be important for antibody recognition since binding is shown for gD having deletion of amino acids 24-32 but not for gD having deletion of amino acids 27-43. Deletion of amino acids 125-161 disrupts antibody recognition. Without wishing to be bound by theory, the deletion of amino acids 125-161 probably disrupts the protein conformation since the deletion disrupts a disulfide bond. Further mapping of the epitope was performed by using gD mutants generated through amino acid substitutions (for example, amino acid substitution of non-alanine amino acid with alanine). Several amino acids were found to be critical for antibody recognition, including Y38, D215, P221, and R222, since substitutions of these amino acids disrupted the recognition by mAb E317 or E425 (FIG. 5).

Therefore, the epitope recognized by mAb E317 or E425 is not a linear epitope and is conformation dependent, and amino acids Y38, D215, P221 and R222 are important for the binding of mAb E317 and E425 to the gD.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for treating or preventing herpes simplex virus (HSV) infection, comprising administering to a subject in need thereof an effective amount of a human antibody that specifically binds to the glycoprotein D (gD) of herpes simplex virus-1 (HSV-1) and herpes simplex virus-2 (HSV-2), wherein the antibody binds to a conformational epitope on the glycoprotein D and interacts with amino acids Y38, D215, P221, and R222 shown in SEQ ID NO:44 or SEQ ID NO:45 or amino acids on the gD corresponding to Y38, D215, P221, and R222 shown in SEQ ID NO:44 or SEQ ID NO:45.

2. The method of claim 1, wherein the subject is at risk of HSV infection.

3. The method of claim 1, wherein the HSV infection is HSV-1 or HSV-2 infection.

4. The method of claim 1, wherein the method further comprises administering another anti-HSV drug.

5. The method of claim 1, wherein the antibody interacts with amino acids 35-40 and 215-222 shown in SEQ ID NO:44 or SEQ ID NO:45 or amino acids on the gD corresponding to amino acids 35-40 and 215-222 shown in SEQ ID NO:44 or SEQ ID NO:45.

6. The method of claim 1, wherein the antibody inhibits reproduction of HSV-1 and/or HSV-2.

7. The method of claim 1, wherein the antibody competes with antibody scFv E317, scFv E425, or scFv Y571 for binding to the gD of HSV-1 and HSV-2, and is able to neutralize HSV-1 and HSV-2 with substantially equivalent potency.

8. The method of claim 1, wherein the antibody comprises a $V_H$ comprising the three complementarity determining regions (CDRs) of the $V_H$ of scFv E317 and a $V_L$ comprising the three CDRs of the $V_L$ of scFv E317.

9. The method of claim 1, wherein the antibody comprises a $V_H$ comprising the amino acids 3-124 of SEQ ID NO:1 and a $V_L$ comprising the amino acids 1-108 of SEQ ID NO:2.

10. The method of claim 1, wherein the antibody comprises the amino acid sequence of SEQ ID NO:5.

11. The method of claim 1, wherein the antibody comprises a $V_H$ comprising the three CDRs of the $V_H$ of scFv E425 and a $V_L$ comprising the three CDRs of the $V_L$ of scFv E425.

12. The method of claim 1, wherein the antibody comprises a $V_H$ comprising the amino acids 3-124 of SEQ ID NO:3 and a $V_L$ comprising the amino acids 1-108 of SEQ ID NO:4.

13. The method of claim 1, wherein the antibody comprises the amino acid sequence of SEQ ID NO:6.

14. The method of claim 1, wherein the antibody comprises the three CDRs from the heavy chain amino acid sequence shown in SEQ ID NO:41, and the three CDRs from the light chain amino acid sequence shown in SEQ ID NO:42.

15. The method of claim 1, wherein the antibody comprises the heavy chain amino acid sequence shown in SEQ ID NO:41, and the light chain amino acid sequence shown in SEQ ID NO:42.

16. The method of claim 1, wherein the antibody comprises the amino acid sequence of SEQ ID NO:43.

17. The method of claim 1, wherein the subject has an HSV infection.

* * * * *

SEQUENCE LISTING

```
<160> NUMBER OF SEQ ID NOS: 45

<210> SEQ ID NO 1
<211> LENGTH: 124
<212> TYPE: PRT
<213> ORGANISM: Homo sapiens
```

<400> SEQUENCE: 1

Met Ala Gln Val Thr Leu Lys Gln Ser Gly Ala Glu Val Lys Lys Pro
1               5                   10                  15

Gly Ser Ser Val Lys Val Ser Cys Thr Ala Ser Gly Gly Thr Leu Arg
            20                  25                  30

Thr Tyr Gly Val Ser Trp Val Arg Gln Ala Pro Gly Gln Gly Leu Glu
        35                  40                  45

Trp Leu Gly Arg Thr Ile Pro Leu Phe Gly Lys Thr Asp Tyr Ala Gln
    50                  55                  60

Lys Phe Gln Gly Arg Val Thr Ile Thr Ala Asp Lys Ser Met Asp Thr
65                  70                  75                  80

Ser Phe Met Glu Leu Thr Ser Leu Thr Ser Glu Asp Thr Ala Val Tyr
                85                  90                  95

Tyr Cys Ala Arg Asp Leu Thr Thr Leu Thr Ser Tyr Asn Trp Trp Asp
            100                 105                 110

Leu Trp Gly Gln Gly Thr Leu Val Thr Val Ser Ser
            115                 120

<210> SEQ ID NO 2
<211> LENGTH: 110
<212> TYPE: PRT
<213> ORGANISM: Homo sapiens

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Gln Leu Ala Trp Tyr Gln Gln Lys Pro Gly Gln Ala Pro Arg Leu Leu
        35                  40                  45

Ile Ser Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gly Gly Thr Lys Val Glu Ile Lys Arg Ala Ala
            100                 105                 110

<210> SEQ ID NO 3
<211> LENGTH: 124
<212> TYPE: PRT
<213> ORGANISM: Homo sapiens

<400> SEQUENCE: 3

Met Ala Gln Val Gln Leu Gln Gln Ser Gly Ala Gly Val Lys Lys Pro
1               5                   10                  15

Gly Ser Ser Val Arg Val Ser Cys Ser Ala Ser Gly Gly Thr Leu Arg
            20                  25                  30

Thr Tyr Ala Leu Ser Trp Val Arg Gln Val Pro Gly Gln Gly Phe Glu
        35                  40                  45

Trp Met Gly Arg Ile Ile Pro Met Phe Gly Lys Thr Asp Tyr Ala Gln
    50                  55                  60

Lys Phe Gln Gly Arg Leu Ser Ile Thr Ala Asp Lys Ser Met Asp Thr
65                  70                  75                  80

Gly Phe Met Glu Leu Thr Ser Leu Thr Ser Glu Asp Thr Ala Val Tyr

```
                    85                  90                  95
Tyr Cys Ala Arg Asp Leu Thr Thr Leu Thr Ser Tyr Asn Trp Leu Asp
                100                 105                 110

Ile Trp Gly Gln Gly Thr Leu Val Thr Val Ser Ser
            115                 120

<210> SEQ ID NO 4
<211> LENGTH: 110
<212> TYPE: PRT
<213> ORGANISM: Homo sapiens

<400> SEQUENCE: 4

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Lys Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Asn Arg Leu Glu
65                  70                  75                  80

Pro Glu Asp Phe Ala Val Tyr Tyr Cys Gln Gln Tyr Gly Arg Ser Pro
                85                  90                  95

Thr Phe Gly Gln Gly Thr Lys Val Glu Ile Lys Arg Ala Ala
            100                 105                 110

<210> SEQ ID NO 5
<211> LENGTH: 245
<212> TYPE: PRT
<213> ORGANISM: Artificial Sequence
<220> FEATURE:
<223> OTHER INFORMATION: Snythetic Construct
<220> FEATURE:
<223> OTHER INFORMATION: Single-chain antibody

<400> SEQUENCE: 5

Gln Val Thr Leu Lys Gln Ser Gly Ala Glu Val Lys Lys Pro Gly Ser
1               5                   10                  15

Ser Val Lys Val Ser Cys Thr Ala Ser Gly Gly Thr Leu Arg Thr Tyr
            20                  25                  30

Gly Val Ser Trp Val Arg Gln Ala Pro Gly Gln Gly Leu Glu Trp Leu
        35                  40                  45

Gly Arg Thr Ile Pro Leu Phe Gly Lys Thr Asp Tyr Ala Gln Lys Phe
    50                  55                  60

Gln Gly Arg Val Thr Ile Thr Ala Asp Lys Ser Met Asp Thr Ser Phe
65                  70                  75                  80

Met Glu Leu Thr Ser Leu Thr Ser Glu Asp Thr Ala Val Tyr Tyr Cys
                85                  90                  95

Ala Arg Asp Leu Thr Thr Leu Thr Ser Tyr Asn Trp Asp Leu Trp
                100                 105                 110

Gly Gln Gly Thr Leu Val Thr Val Ser Ser Gly Gly Gly Gly Ser Gly
            115                 120                 125

Gly Gly Gly Ser Gly Gly Gly Ser Glu Ile Val Leu Thr Gln Ser
        130                 135                 140

Pro Gly Thr Leu Ser Leu Ser Pro Gly Glu Arg Ala Thr Leu Ser Cys
145                 150                 155                 160

Arg Ala Ser Gln Ser Val Thr Ser Ser Gln Leu Ala Trp Tyr Gln Gln
```

```
            165                 170                 175
Lys Pro Gly Gln Ala Pro Arg Leu Leu Ile Ser Gly Ala Ser Asn Arg
            180                 185                 190

Ala Thr Gly Ile Pro Asp Arg Phe Ser Gly Ser Gly Ser Gly Thr Asp
            195                 200                 205

Phe Thr Leu Thr Ile Ser Arg Leu Glu Pro Glu Asp Phe Ala Val Tyr
            210                 215                 220

Tyr Cys Gln Gln Tyr Gly Ser Ser Pro Thr Phe Gly Gly Gly Thr Lys
225                 230                 235                 240

Val Glu Ile Lys Arg
                245

<210> SEQ ID NO 6
<211> LENGTH: 245
<212> TYPE: PRT
<213> ORGANISM: Artificial Sequence
<220> FEATURE:
<223> OTHER INFORMATION: Snythetic Construct
<220> FEATURE:
<223> OTHER INFORMATION: Single-chain antibody

<400> SEQUENCE: 6

Gln Val Gln Leu Gln Gln Ser Gly Ala Gly Val Lys Lys Pro Gly Ser
1               5                   10                  15

Ser Val Arg Val Ser Cys Ser Ala Ser Gly Gly Thr Leu Arg Thr Tyr
            20                  25                  30

Ala Leu Ser Trp Val Arg Gln Val Pro Gly Gln Gly Phe Glu Trp Met
        35                  40                  45

Gly Arg Ile Ile Pro Met Phe Gly Lys Thr Asp Tyr Ala Gln Lys Phe
    50                  55                  60

Gln Gly Arg Leu Ser Ile Thr Ala Asp Lys Ser Met Asp Thr Gly Phe
65                  70                  75                  80

Met Glu Leu Thr Ser Leu Thr Ser Glu Asp Thr Ala Val Tyr Tyr Cys
                85                  90                  95

Ala Arg Asp Leu Thr Thr Leu Thr Ser Tyr Asn Trp Leu Asp Ile Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Glu Thr Thr Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Val Ser Ser Asn Tyr Leu Ala Trp Tyr Gln Lys
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
            195                 200                 205

Phe Thr Leu Thr Ile Asn Arg Leu Glu Pro Glu Asp Phe Ala Val Tyr
            210                 215                 220

Tyr Cys Gln Gln Tyr Gly Arg Ser Pro Thr Phe Gly Gln Gly Thr Lys
225                 230                 235                 240

Val Glu Ile Lys Arg
                245

<210> SEQ ID NO 7
<211> LENGTH: 56
```

```
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 7
gtcctcgcaa ctgcggccca gccggccatg gcccaggtgc agctggtgsa rtctgg        56

<210> SEQ ID NO 8
<211> LENGTH: 56
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 8
gtcctcgcaa ctgcggccca gccggccatg gcccaggtca acttaaggga gtctgg        56

<210> SEQ ID NO 9
<211> LENGTH: 54
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 9
gtcctcgcaa ctgcggccca gccggccatg gccgaggtgc agctgktgga gwcy          54

<210> SEQ ID NO 10
<211> LENGTH: 55
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 10
gtcctcgcaa ctgcggccca gccggccatg gcccaggtgc agctgcagga gtcsg         55

<210> SEQ ID NO 11
<211> LENGTH: 56
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 11
gtcctcgcaa ctgcggccca gccggccatg gccgaggtgc agctgttgca gtctgc        56

<210> SEQ ID NO 12
<211> LENGTH: 54
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 12
gtcctcgcaa ctgcggccca gccggccatg gcccaggtac agctgcagca gtca          54
```

<210> SEQ ID NO 13
<211> LENGTH: 55
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 13
gtcctcgcaa ctgcggccca gccggccatg gcccagrtca ccttgaagga gtctg         55

<210> SEQ ID NO 14
<211> LENGTH: 55
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 14
gtcctcgcaa ctgcggccca gccggccatg gcccaggtgc agctacagca gtggg         55

<210> SEQ ID NO 15
<211> LENGTH: 24
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 15
tgaggagacg gtgaccaggg tgcc                                            24

<210> SEQ ID NO 16
<211> LENGTH: 24
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 16
tgaagagacg gtgaccattg tccc                                            24

<210> SEQ ID NO 17
<211> LENGTH: 24
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 17
tgaggagacg gtgaccaggg ttcc                                            24

<210> SEQ ID NO 18
<211> LENGTH: 24
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 18
tgaggagacg gtgaccgtgg tccc                                          24

<210> SEQ ID NO 19
<211> LENGTH: 23
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 19
gacatccaga tgacccagtc tcc                                           23

<210> SEQ ID NO 20
<211> LENGTH: 23
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 20
gatgttgtga tgactcagtc tcc                                           23

<210> SEQ ID NO 21
<211> LENGTH: 23
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 21
gaaattgtgt tgacgcagtc tcc                                           23

<210> SEQ ID NO 22
<211> LENGTH: 23
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 22
gacatcgtga tgacccagtc tcc                                           23

<210> SEQ ID NO 23
<211> LENGTH: 23
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 23
gaaacgacac tcacgcagtc tcc                                           23

<210> SEQ ID NO 24
<211> LENGTH: 23
<212> TYPE: DNA
<213> ORGANISM: Artificial Sequence

```
<220> FEATURE:
<223> OTHER INFORMATION: Snythetic Construct
<220> FEATURE:
<223> OTHER INFORMATION: Primer

<400> SEQUENCE: 24
gaaattgtgc tgactcagtc tcc                                              23

<210> SEQ ID NO 25
<211> LENGTH: 48
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 25
gagtcattct cgacttgcgg ccgcacgttt gatttccacc ttggtccc                   48

<210> SEQ ID NO 26
<211> LENGTH: 48
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 26
gagtcattct cgacttgcgg ccgcacgttt gatctccagc ttggtccc                   48

<210> SEQ ID NO 27
<211> LENGTH: 48
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 27
gagtcattct cgacttgcgg ccgcacgttt gatatccact ttggtccc                   48

<210> SEQ ID NO 28
<211> LENGTH: 48
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 28
gagtcattct cgacttgcgg ccgcacgttt gatctccacc ttggtccc                   48

<210> SEQ ID NO 29
<211> LENGTH: 48
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 29
gagtcattct cgacttgcgg ccgcacgttt aatctccagt cgtgtccc                   48
```

```
<210> SEQ ID NO 30
<211> LENGTH: 23
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 30
cagtctgtgt tgacgcagcc gcc                                              23

<210> SEQ ID NO 31
<211> LENGTH: 23
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 31
cagtctgccc tgactcagcc tgc                                              23

<210> SEQ ID NO 32
<211> LENGTH: 23
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 32
tcctatgtgc tgactcagcc acc                                              23

<210> SEQ ID NO 33
<211> LENGTH: 23
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 33
tcttctgagc tgactcagga ccc                                              23

<210> SEQ ID NO 34
<211> LENGTH: 23
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 34
cacgttatac tgactcaacc gcc                                              23

<210> SEQ ID NO 35
<211> LENGTH: 23
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 35
```
caggctgtgc tcactcagcc gtc                                          23

<210> SEQ ID NO 36
<211> LENGTH: 23
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 36
aattttatgc tgactcagcc cca                                          23

<210> SEQ ID NO 37
<211> LENGTH: 48
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 37
gagtcattct cgacttgcgg ccgcacctag gacggtgacc ttggtccc               48

<210> SEQ ID NO 38
<211> LENGTH: 48
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 38
gagtcattct cgacttgcgg ccgcacctag gacggtcagc ttggtccc               48

<210> SEQ ID NO 39
<211> LENGTH: 48
<212> TYPE: DNA
<213> ORGANISM: Artificial Sequence
<220> FEATURE:
<223> OTHER INFORMATION: Snythetic Construct
<220> FEATURE:
<223> OTHER INFORMATION: Primer

<400> SEQUENCE: 39
gagtcattct cgacttgcgg ccgcacctaa aacggtgagc tgggtccc               48

<210> SEQ ID NO 40
<211> LENGTH: 45
<212> TYPE: DNA
<213> ORGANISM: Artificial Sequence
<220> FEATURE:
<223> OTHER INFORMATION: Snythetic Construct
<220> FEATURE:
<223> OTHER INFORMATION: linker sequence

<400> SEQUENCE: 40
ggtggaggcg gttcaggcgg aggtggctct ggcggtggcg gatcg                  45

<210> SEQ ID NO 41
<211> LENGTH: 122
<212> TYPE: PRT
<213> ORGANISM: Homo sapiens

<400> SEQUENCE: 41

```
Gln Val Gln Leu Gln Gln Ser Gly Ala Glu Val Lys Lys Pro Gly Ser
 1               5                  10                  15

Ser Val Lys Val Ser Cys Lys Ala Ser Gly Gly Thr Leu Arg Thr Tyr
            20                  25                  30

Gly Val Ser Trp Val Arg Gln Ala Pro Gly Gln Gly Leu Glu Trp Leu
        35                  40                  45

Gly Gly Thr Ile Pro Leu Phe Gly Lys Thr Asp Tyr Ala Gln Lys Phe
    50                  55                  60

Gln Gly Arg Val Thr Ile Thr Ala Asp Lys Ser Met Asp Thr Ser Phe
65                  70                  75                  80

Met Glu Leu Thr Ser Leu Thr Ser Glu Asp Thr Ala Val Tyr Tyr Cys
                85                  90                  95

Ala Arg Asp Leu Thr Thr Leu Thr Ser Tyr Asn Trp Trp Asp Leu Trp
            100                 105                 110

Gly Gln Gly Thr Leu Val Thr Val Ser Ser
        115                 120
```

<210> SEQ ID NO 42
<211> LENGTH: 109
<212> TYPE: PRT
<213> ORGANISM: Homo sapiens

<400> SEQUENCE: 42

```
Glu Thr Thr Leu Thr Gln Ser Pro Gly Ile Leu Ser Leu Ser Pro Gly
 1               5                  10                  15

Asp Arg Ala Thr Leu Ser Cys Arg Ala Ser Gln Ser Val Gly Ser Val
            20                  25                  30

Asn Leu Ala Trp Tyr Gln Gln Arg Pro Gly Gln Ala Pro Arg Leu Leu
        35                  40                  45

Ile His Gly Ala Ser Asn Arg Ala Thr Gly Ile Pro Asp Arg Phe Ser
    50                  55                  60

Gly Val Gly Ser Gly Thr Asp Phe Thr Leu Thr Ile Asn Arg Leu Glu
65                  70                  75                  80

Pro Asp Asp Phe Ala Val Tyr Tyr Cys Gln Gln Tyr Gly Thr Ser Pro
                85                  90                  95

Ile Thr Phe Gly Gln Gly Thr Arg Leu Glu Ile Lys Arg
            100                 105
```

<210> SEQ ID NO 43
<211> LENGTH: 246
<212> TYPE: PRT
<213> ORGANISM: Artificial Sequence
<220> FEATURE:
<223> OTHER INFORMATION: Snythetic Construct
<220> FEATURE:
<223> OTHER INFORMATION: Single-chain Antibody

<400> SEQUENCE: 43

```
Gln Val Gln Leu Gln Gln Ser Gly Ala Glu Val Lys Lys Pro Gly Ser
 1               5                  10                  15

Ser Val Lys Val Ser Cys Lys Ala Ser Gly Gly Thr Leu Arg Thr Tyr
            20                  25                  30

Gly Val Ser Trp Val Arg Gln Ala Pro Gly Gln Gly Leu Glu Trp Leu
        35                  40                  45

Gly Gly Thr Ile Pro Leu Phe Gly Lys Thr Asp Tyr Ala Gln Lys Phe
    50                  55                  60

Gln Gly Arg Val Thr Ile Thr Ala Asp Lys Ser Met Asp Thr Ser Phe
65                  70                  75                  80
```

```
Met Glu Leu Thr Ser Leu Thr Ser Glu Asp Thr Ala Val Tyr Tyr Cys
                85                  90                  95

Ala Arg Asp Leu Thr Thr Leu Thr Ser Tyr Asn Trp Trp Asp Leu Trp
            100                 105                 110

Gly Gln Gly Thr Leu Val Thr Val Ser Ser Gly Gly Gly Gly Ser Gly
            115                 120                 125

Gly Gly Gly Ser Gly Gly Gly Ser Glu Thr Thr Leu Thr Gln Ser
130                 135                 140

Pro Gly Ile Leu Ser Leu Ser Pro Gly Asp Arg Ala Thr Leu Ser Cys
145                 150                 155                 160

Arg Ala Ser Gln Ser Val Gly Ser Val Asn Leu Ala Trp Tyr Gln Gln
                165                 170                 175

Arg Pro Gly Gln Ala Pro Arg Leu Leu Ile His Gly Ala Ser Asn Arg
            180                 185                 190

Ala Thr Gly Ile Pro Asp Arg Phe Ser Gly Val Gly Ser Gly Thr Asp
            195                 200                 205

Phe Thr Leu Thr Ile Asn Arg Leu Glu Pro Asp Asp Phe Ala Val Tyr
            210                 215                 220

Tyr Cys Gln Gln Tyr Gly Thr Ser Pro Ile Thr Phe Gly Gln Gly Thr
225                 230                 235                 240

Arg Leu Glu Ile Lys Arg
                245

<210> SEQ ID NO 44
<211> LENGTH: 369
<212> TYPE: PRT
<213> ORGANISM: Artificial Sequence
<220> FEATURE:
<223> OTHER INFORMATION: Snythetic Construct
<220> FEATURE:
<223> OTHER INFORMATION: herpes simplex virus protein sequence

<400> SEQUENCE: 44

Lys Tyr Ala Leu Ala Asp Ala Ser Leu Lys Met Ala Asp Pro Asn Arg
1               5                   10                  15

Phe Arg Gly Lys Asp Leu Pro Val Leu Asp Gln Leu Thr Asp Pro Pro
            20                  25                  30

Gly Val Arg Arg Val Tyr His Ile Gln Ala Gly Leu Pro Asp Pro Phe
            35                  40                  45

Gln Pro Pro Ser Leu Pro Ile Thr Val Tyr Tyr Ala Val Leu Glu Arg
        50                  55                  60

Ala Cys Arg Ser Val Leu Leu Asn Ala Pro Ser Glu Ala Pro Gln Ile
65              70                  75                  80

Val Arg Gly Ala Ser Glu Asp Val Arg Lys Gln Pro Tyr Asn Leu Thr
                85                  90                  95

Ile Ala Trp Phe Arg Met Gly Gly Asn Cys Ala Ile Pro Ile Thr Val
            100                 105                 110

Met Glu Tyr Thr Glu Cys Ser Tyr Asn Lys Ser Leu Gly Ala Cys Pro
            115                 120                 125

Ile Arg Thr Gln Pro Arg Trp Asn Tyr Tyr Asp Ser Phe Ser Ala Val
            130                 135                 140

Ser Glu Asp Asn Leu Gly Phe Leu Met His Ala Pro Ala Phe Glu Thr
145                 150                 155                 160

Ala Gly Thr Tyr Leu Arg Leu Val Lys Ile Asn Asp Trp Thr Glu Ile
                165                 170                 175

Thr Gln Phe Ile Leu Glu His Arg Ala Lys Gly Ser Cys Lys Tyr Ala
```

```
                      180                 185                 190
Leu Pro Leu Arg Ile Pro Pro Ser Ala Cys Leu Ser Pro Gln Ala Tyr
                195                 200                 205
Gln Gln Gly Val Thr Val Asp Ser Ile Gly Met Leu Pro Arg Phe Ile
            210                 215                 220
Pro Glu Asn Gln Arg Thr Val Ala Val Tyr Ser Leu Lys Ile Ala Gly
225                 230                 235                 240
Trp His Gly Pro Lys Ala Pro Tyr Thr Ser Thr Leu Leu Pro Pro Glu
                245                 250                 255
Leu Ser Glu Thr Pro Asn Ala Thr Gln Pro Glu Leu Ala Pro Glu Asp
            260                 265                 270
Pro Glu Asp Ser Ala Leu Leu Glu Asp Pro Val Gly Thr Val Ala Pro
        275                 280                 285
Gln Ile Pro Pro Asn Trp His Ile Pro Ser Ile Gln Asp Ala Ala Thr
        290                 295                 300
Pro Tyr His Pro Ala Thr Pro Asn Asn Met Gly Leu Ile Ala Gly
305                 310                 315                 320
Ala Val Gly Gly Ser Leu Leu Ala Ala Leu Val Ile Cys Gly Ile Val
                325                 330                 335
Tyr Trp Met His Arg Arg Thr Arg Lys Ala Pro Lys Arg Ile Arg Leu
                340                 345                 350
Pro His Ile Arg Glu Asp Asp Gln Pro Ser Ser His Gln Pro Leu Phe
            355                 360                 365
Tyr

<210> SEQ ID NO 45
<211> LENGTH: 368
<212> TYPE: PRT
<213> ORGANISM: Artificial Sequence
<220> FEATURE:
<223> OTHER INFORMATION: Snythetic Construct
<220> FEATURE:
<223> OTHER INFORMATION: herpes simplex virus protein sequences

<400> SEQUENCE: 45

Lys Tyr Ala Leu Ala Asp Pro Ser Leu Lys Met Ala Asp Pro Asn Arg
1               5                   10                  15
Phe Arg Gly Lys Asn Leu Pro Val Leu Asp Gln Leu Thr Asp Pro Pro
            20                  25                  30
Gly Val Lys Arg Val Tyr His Ile Gln Pro Ser Leu Glu Asp Pro Phe
        35                  40                  45
Gln Pro Pro Ser Ile Pro Ile Thr Val Tyr Tyr Ala Val Leu Glu Arg
    50                  55                  60
Ala Cys Arg Ser Val Leu Leu His Ala Pro Ser Glu Ala Pro Gln Ile
65                  70                  75                  80
Val Arg Gly Ala Ser Asp Glu Ala Arg Lys His Thr Tyr Asn Leu Thr
                85                  90                  95
Ile Ala Trp Tyr Arg Met Gly Asp Asn Cys Ala Ile Pro Ile Thr Val
            100                 105                 110
Met Glu Tyr Thr Glu Cys Pro Tyr Asn Lys Ser Leu Gly Val Cys Pro
        115                 120                 125
Ile Arg Thr Gln Pro Arg Trp Ser Tyr Tyr Asp Ser Phe Ser Ala Val
    130                 135                 140
Ser Glu Asp Asn Leu Gly Phe Leu Met His Ala Pro Ala Phe Glu Thr
145                 150                 155                 160
Ala Gly Thr Tyr Leu Arg Leu Val Lys Ile Asn Asp Trp Thr Glu Ile
```

-continued

```
                        165                 170                 175
Thr Gln Phe Ile Leu Glu His Arg Ala Arg Ala Ser Cys Lys Tyr Ala
            180                 185                 190

Leu Pro Leu Arg Ile Pro Pro Ala Ala Cys Leu Thr Ser Lys Ala Tyr
            195                 200                 205

Gln Gln Gly Val Thr Val Asp Ser Ile Gly Met Leu Pro Arg Phe Ile
            210                 215                 220

Pro Glu Asn Gln Arg Thr Val Ala Leu Tyr Ser Leu Lys Ile Ala Gly
225                 230                 235                 240

Trp His Gly Pro Lys Pro Pro Tyr Thr Ser Thr Leu Leu Pro Pro Glu
            245                 250                 255

Leu Ser Asp Thr Thr Asn Ala Thr Gln Pro Glu Leu Val Pro Glu Asp
            260                 265                 270

Pro Glu Asp Ser Ala Leu Leu Glu Asp Pro Ala Gly Thr Val Ser Ser
            275                 280                 285

Gln Ile Pro Pro Asn Trp His Ile Pro Ser Ile Gln Asp Val Ala Pro
            290                 295                 300

His His Ala Pro Ala Ala Pro Ser Asn Pro Gly Leu Ile Ile Gly Ala
305                 310                 315                 320

Leu Ala Gly Ser Thr Leu Ala Val Leu Val Ile Gly Gly Ile Ala Phe
                325                 330                 335

Trp Val Arg Arg Arg Ala Gln Met Ala Pro Lys Arg Leu Arg Leu Pro
            340                 345                 350

His Ile Arg Asp Asp Asp Ala Pro Pro Ser His Gln Pro Leu Phe Tyr
            355                 360                 365
```